US011309060B2

(12) United States Patent
Janevski et al.

(10) Patent No.: US 11,309,060 B2
(45) Date of Patent: Apr. 19, 2022

(54) SYSTEM AND METHOD FOR REAL TIME CLINICAL QUESTIONS PRESENTATION AND MANAGEMENT

(71) Applicant: KONINKLIJKE PHILIPS N.V., Eindhoven (NL)

(72) Inventors: Angel Janevski, New York, NY (US); Sitharthan Kamalakaran, Pelham, NY (US); Nilanjana Banerjee, Armonk, NY (US); Vinay Varadan, New York, NY (US); Nevenka Dimitrova, Pelham Manor, NY (US); Mine Danisman Tasar, Noord Brabant (NL)

(73) Assignee: Koninklijke Philips N.V., Eindhoven (NL)

( * ) Notice: Subject to any disclaimer, the term of this patent is extended or adjusted under 35 U.S.C. 154(b) by 1114 days.

(21) Appl. No.: 14/312,743

(22) Filed: Jun. 24, 2014

(65) Prior Publication Data

US 2014/0379379 A1    Dec. 25, 2014

Related U.S. Application Data

(60) Provisional application No. 61/838,361, filed on Jun. 24, 2013.

(51) Int. Cl.
*G16B 20/20* (2019.01)
*G16B 30/00* (2019.01)
(Continued)

(52) U.S. Cl.
CPC .............. *G16B 20/20* (2019.02); *G16B 20/10* (2019.02); *G16B 30/00* (2019.02); *G16B 30/10* (2019.02);
(Continued)

(58) Field of Classification Search
CPC ........ G06F 19/322; G06F 19/18; G06F 19/36; G06F 19/34; G06Q 50/24; G06Q 50/22;
(Continued)

(56) References Cited

U.S. PATENT DOCUMENTS 5,574,828 A * 11/1996 Hayward .............. G06F 19/325
706/45
6,970,791 B1   11/2005 Potter et al.
(Continued)

FOREIGN PATENT DOCUMENTS

WO     WO-0169513 A2 *   9/2001  ............. G16H 50/30
WO        2010024894 A1    3/2010

OTHER PUBLICATIONS

PLOSGeneticsOPCPCPGCancer—Chia Huey Ooi, Tatiana Ivanova, Jeanie Wu, Others, Oncogenic Pathway Combinations Predict Clinical Prognosis in Gastric Cancer, Oct. 2009, PLOS Genetics, vol. 10, Issue 10 (All Pages).*

(Continued)

*Primary Examiner* — Beth V Boswell
*Assistant Examiner* — Teresa S Williams

(57) ABSTRACT

In a clinical decision support method, outputs of computer-implemented analytical modules are computed for a patient. Information is displayed for the patient pertaining to a clinical question comprising outputs computed for the patient of analytical modules associated with the clinical question. The analytical modules may include modules configured to perform in silico genetic/genomic tests using genetic/genome sequencing (whole genome, whole exome, whole transcriptome, targeted gene panels, etc) or microarray data. A clinical question-module matrix (CQ-M matrix) may be generated for the patient associating clinical questions with analytical modules, and the method may further include populating the clinical questions with outputs computed for the patient of the analytical modules associated with the clinical questions by the CQ-M matrix. Such populating advantageously re-uses outputs computed for the patient when an analytical module is associated with two or more different clinical questions by the CQ-M matrix. This system empowers the clinician to focus on the clinical (Continued)

Figure 1:
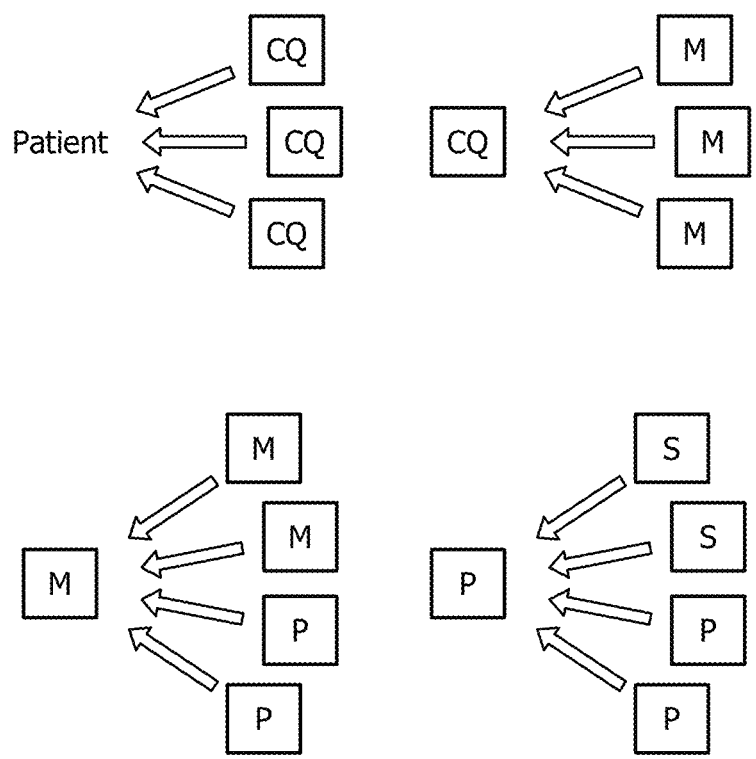

aspects of patient management while allowing the data complexities of patient genomic data interpretation to be handled by the clinical decision support system.

30 Claims, 15 Drawing Sheets

(51) Int. Cl.
*G16H 10/20* (2018.01)
*G16H 50/20* (2018.01)
*G16B 50/00* (2019.01)
*G16B 30/10* (2019.01)
*G16B 50/30* (2019.01)
*G16B 20/10* (2019.01)
*G16B 20/00* (2019.01)

(52) U.S. Cl.
CPC .............. *G16B 50/00* (2019.02); *G16B 50/30* (2019.02); *G16H 10/20* (2018.01); *G16H 50/20* (2018.01); *G16B 20/00* (2019.02)

(58) Field of Classification Search
CPC ........ G16H 10/20; G16H 10/60; G16H 50/20; G16H 10/40; G16H 20/00; G16H 50/70; G16H 40/20; G16H 20/10; G16H 70/60; G16B 30/00; G16B 30/10; G16B 50/00
USPC .......................................... 705/3, 2
See application file for complete search history.

(56) References Cited

U.S. PATENT DOCUMENTS

| | | | |
|---|---|---|---|
| 8,365,065 B2* | 1/2013 | Gejdos | G06F 19/3487 715/215 |
| 9,092,391 B2* | 7/2015 | Stephan | G06F 19/18 |
| 9,224,224 B2* | 12/2015 | Harder | G06F 19/3406 |
| 2002/0099570 A1* | 7/2002 | Knight | G06F 19/322 705/2 |
| 2003/0108938 A1* | 6/2003 | Pickar | G06F 19/322 435/6.11 |
| 2003/0163488 A1* | 8/2003 | Kloos | G16H 70/40 |
| 2004/0122707 A1* | 6/2004 | Sabol | G06F 19/322 705/2 |
| 2007/0118399 A1* | 5/2007 | Avinash | G06F 19/322 705/2 |
| 2007/0271604 A1 | 11/2007 | Webster et al. | |
| 2008/0221923 A1* | 9/2008 | Shogan | G06F 19/00 705/2 |
| 2009/0259489 A1 | 10/2009 | Kimura et al. | |
| 2010/0174555 A1* | 7/2010 | Abraham-Fuchs | G06F 19/328 705/3 |
| 2011/0060604 A1* | 3/2011 | Bangara | G06F 19/322 705/2 |
| 2011/0153361 A1* | 6/2011 | Hanina | G06Q 10/10 705/3 |
| 2013/0226621 A1* | 8/2013 | Van Der Zaag | G06Q 50/22 705/3 |
| 2014/0032125 A1* | 1/2014 | Hawkins | G06F 19/28 702/19 |
| 2014/0330583 A1* | 11/2014 | Madhavan | G06F 19/28 705/3 |

OTHER PUBLICATIONS

Rebecca Mercieca-Bebber, Madeleine T King, Melanie J Calvert, Martin Stockler, Michael Friedlander, The importance of patient-reported outcomes (PRO) in clinical trials and strategies for future optimization, Dovepress, Patient Related Outcome Measures, 2018, pp. 353-367 (Year: 2018).*

\* cited by examiner

FIG. 9

SYSTEM AND METHOD FOR REAL TIME CLINICAL QUESTIONS PRESENTATION AND MANAGEMENT

The following relates to the patient care arts, clinical decision support arts, and related arts.

Medical professionals today have the luxury of access to an abundance of medical data. The human genome is composed of roughly $3 \times 10^9$ nucleotides collectively encoding approximately 23,000 genes, and high speed genetic sequencing technologies can make this whole genome sequence available for healthy patient tissue, along with corresponding whole genome sequence data for malignant tissue. Next generation sequencing (or equivalent high throughput technologies) can generate tens of thousands of data points relating to gene expression or other molecular marker levels in healthy and malignant tissue. In the case of oncology, where the root cause of disease is typically genetic in nature, molecular data can be of fundamental importance for patient diagnosis and treatment monitoring. Other informational sources such as histopathology and medical imaging provide information supplemental or complementary to the molecular data.

However, this abundance of medical data is also a burden on medical personnel, who can be overwhelmed with data overload.

Automated clinical decision support system designers strive to optimize the level of detail in the information considered based on other constraints that exist in the clinical workflow. Informatics solutions focusing on data management and access in the clinic typically aim at structured storage and access of data, while at the same time employing anonymization and/or limits on data access as appropriate to maintain patient privacy. However, existing clinical decision support systems ultimately can be a straightjacket that limits treatment flexibility. For example, a clinical workflow can be useful in guiding medical personnel to the correct diagnosis—but constraining the clinical workflow to the guideline may lead away from the correct diagnosis in unusual patient cases that do not align with the automated clinical workflow.

Existing clinical decision support systems can also produce delays in the treatment process. The step-by-step nature of a clinical workflow enforces discipline in the process of diagnosis and treatment, which is usually advantageous. However, it also can lead to a bottleneck that delays treatment. For example, treatment may be delayed while a laboratory schedules, performs, and reports results of a molecular test that is used in a diagnostic step of the workflow.

In summary, broad molecular profiles provided by sequencing technologies enable virtually unlimited number of analyses to be at the disposal of the clinician enabling exploration of diagnosis and treatment options. Some of these operations are not trivial to capture as guidelines and alternative methods may streamline effective utilization of clinical data. The following contemplates improved apparatuses and methods that overcome the aforementioned limitations and others.

According to one illustrative aspect, a non-transitory storage medium stores instructions executable by an electronic data processing device to perform a clinical decision support method including: associating computer-implemented analytical modules with clinical questions; computing outputs of computer-implemented analytical modules for a patient; and displaying information for the patient pertaining to a clinical question comprising outputs computed for the patient of the computer-implemented analytical modules associated with the clinical question. The computer-implemented analytical modules suitably include a plurality of computer-implemented analytical modules configured to perform in silico genetic tests using genetic sequencing or microarray data or proteomics data or analyze or retrieve other patient data from other data sources. The associating may comprise instantiating a clinical question-module matrix (CQ-M) association data structure for the patient associating clinical questions and computer-implemented analytical modules. The clinical decision support method may further comprise populating the clinical questions with outputs computed for the patient of the computer-implemented analytical modules, wherein the populating re-uses outputs computed for the patient when a computer-implemented analytical module is associated with two or more different clinical questions by the CQ-M data structure for the patient. The CQ-M matrix for the patient may be instituted by copying a template CQ-M data structure defined for a clinical condition and a relevant group of patients.

According to another illustrative aspect, an apparatus comprises an electronic data processing device and a non-transitory storage medium as set forth in the immediately preceding paragraph, wherein the electronic data processing device is configured to read and execute the instructions stored on the non-transitory storage medium to perform the clinical decision support method.

According to another illustrative aspect, a clinical decision support method comprises: computing outputs for a patient of a plurality of computer-implemented analytical modules associated with clinical questions; displaying a list of the clinical questions; receiving a selection of a listed clinical question; and displaying information for the patient pertaining to the selected clinical question comprising outputs computed for the patient of one or more computer-implemented analytical modules associated with the selected clinical question. The computer-implemented analytical modules may include a plurality of computer-implemented analytical modules configured to perform in silico genetic tests or analysis or retrieval of other patient data. The clinical decision support method may further comprise generating a clinical question-module matrix (CQ-M matrix, or a similar CQ-M association data structure) for the patient having one of rows and columns representing the clinical questions and the other of rows and columns representing the computer-implemented analytical modules, and the one or more computer-implemented analytical modules associated with the clinical question are determined using the CQ-M matrix for the patient. The CQ-M matrix for the patient may be generated by copying a default CQ-M matrix, and the method may further comprise receiving a modification of the CQ-M matrix for the patient from a user by displaying two or more display areas containing icons representing computer-implemented analytical modules of different categories, receiving a drag-and-drop operation transferring an icon from one display area to another display area, and determining the modification of the CQ-M matrix for the patient based on the received drag-and-drop operation. Other user operations may result in modification of the CQ-M matrix. For example, user action based on the data from an analytical module may change its state in the CQ-M matrix. Establishing or removing a relation between two or more analytical modules will also result in an updated CQ-M matrix. Still further, data from new or updated analytical modules in the background may also invoke update of the CQ-M matrix.

One advantage resides in providing clinical decision support focused on addressing clinical questions.

Another advantage resides in providing a clinical decision support system configured to re-use analytical modules to address different clinical questions. A further advantage is the consistent view of analytical modules and clinical questions continuously updated with user actions and data.

Another advantage resides in pre-computing analytical modules as described in the CQ-M matrix or equivalent representation of the relevant analytical modules and clinical questions.

Another advantage resides in providing a clinical decision support system with a user interface configurable by the clinician to include analyses chosen by the clinician.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a generalized topology of the illustrative clinical decision support (CDS) system disclosed herein.

Figure 2:
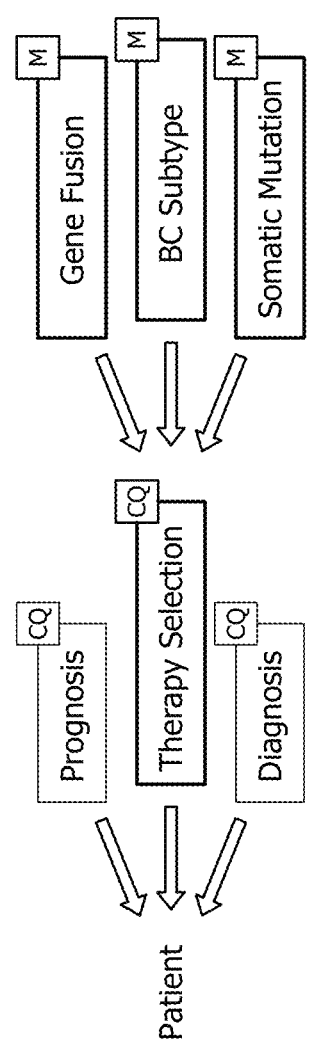
Figure 3:
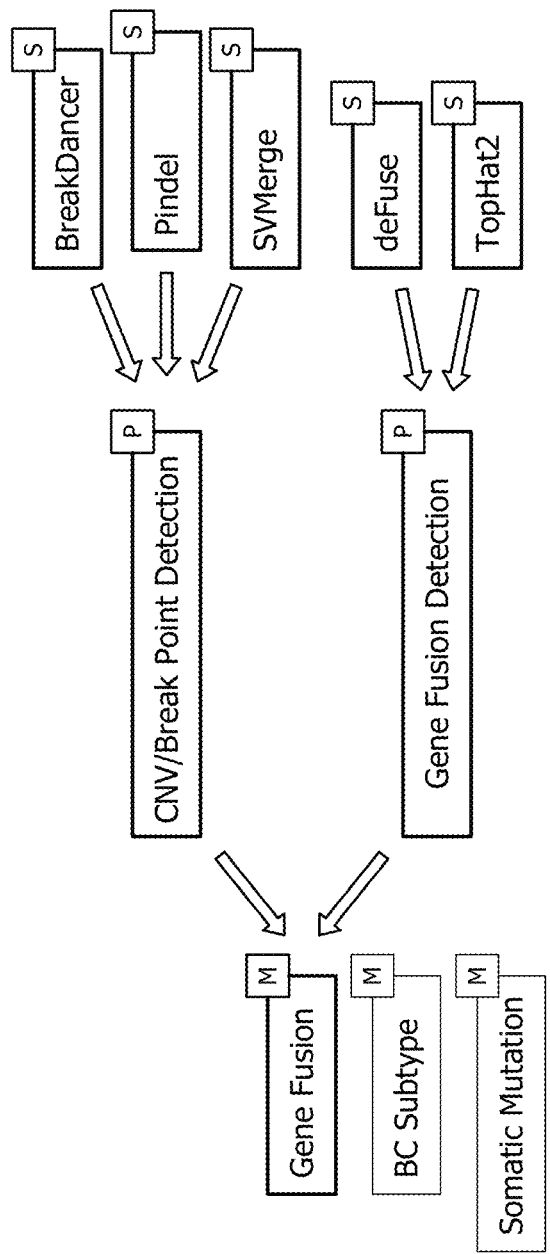

FIGS. 2 and 3 diagrammatically show the CDS system topology associated with a Gene Fusion module.

Figures 4, 5:
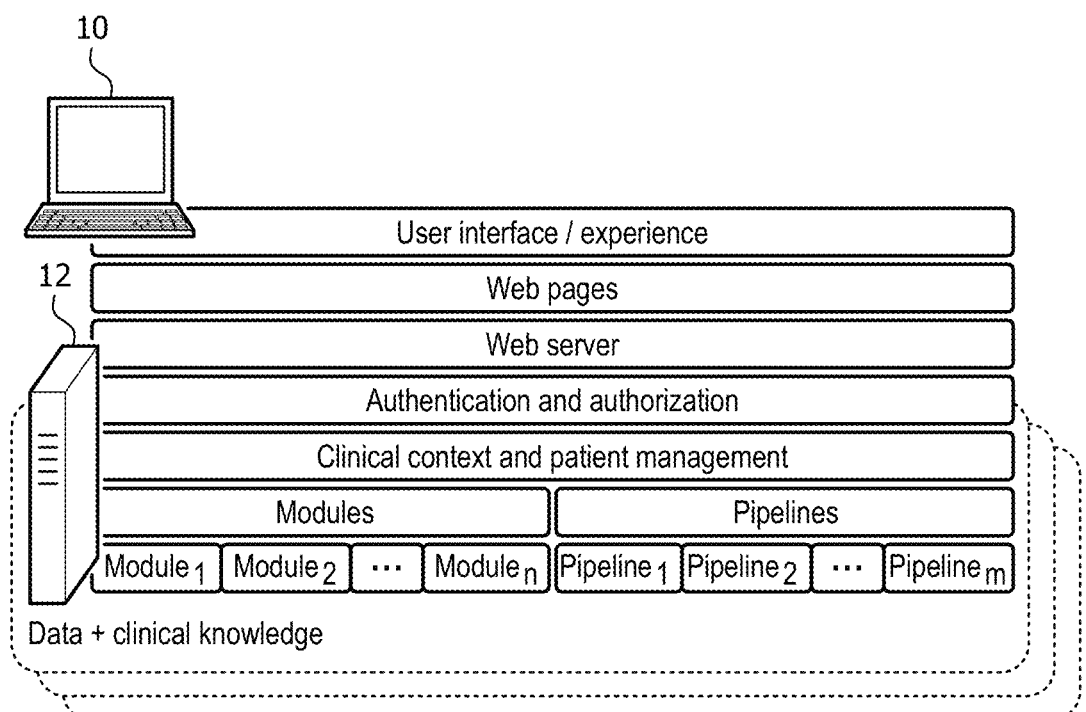

FIG. 4 diagrammatically shows a clinical question-analytical module matrix (CQ-M matrix) employed in clinical decision support systems disclosed herein.

FIG. 5 diagrammatically shows a clinical decision support system architecture employing a web browser-based user interface.

Figure 6:
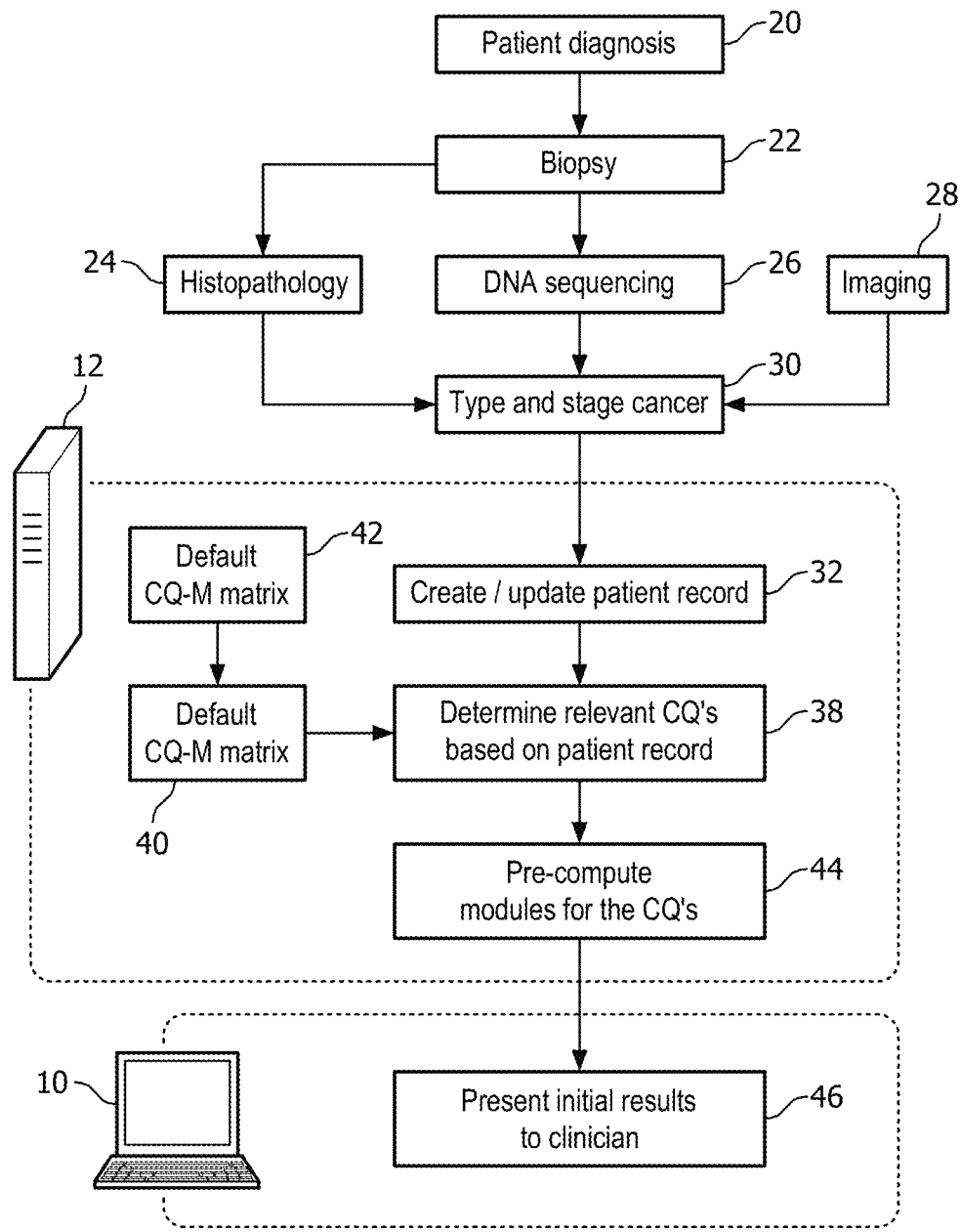

FIG. 6 diagrammatically shows patient setup processing performed by a clinical decision support system as disclosed herein in the context of patient workflow.

Figure 7:
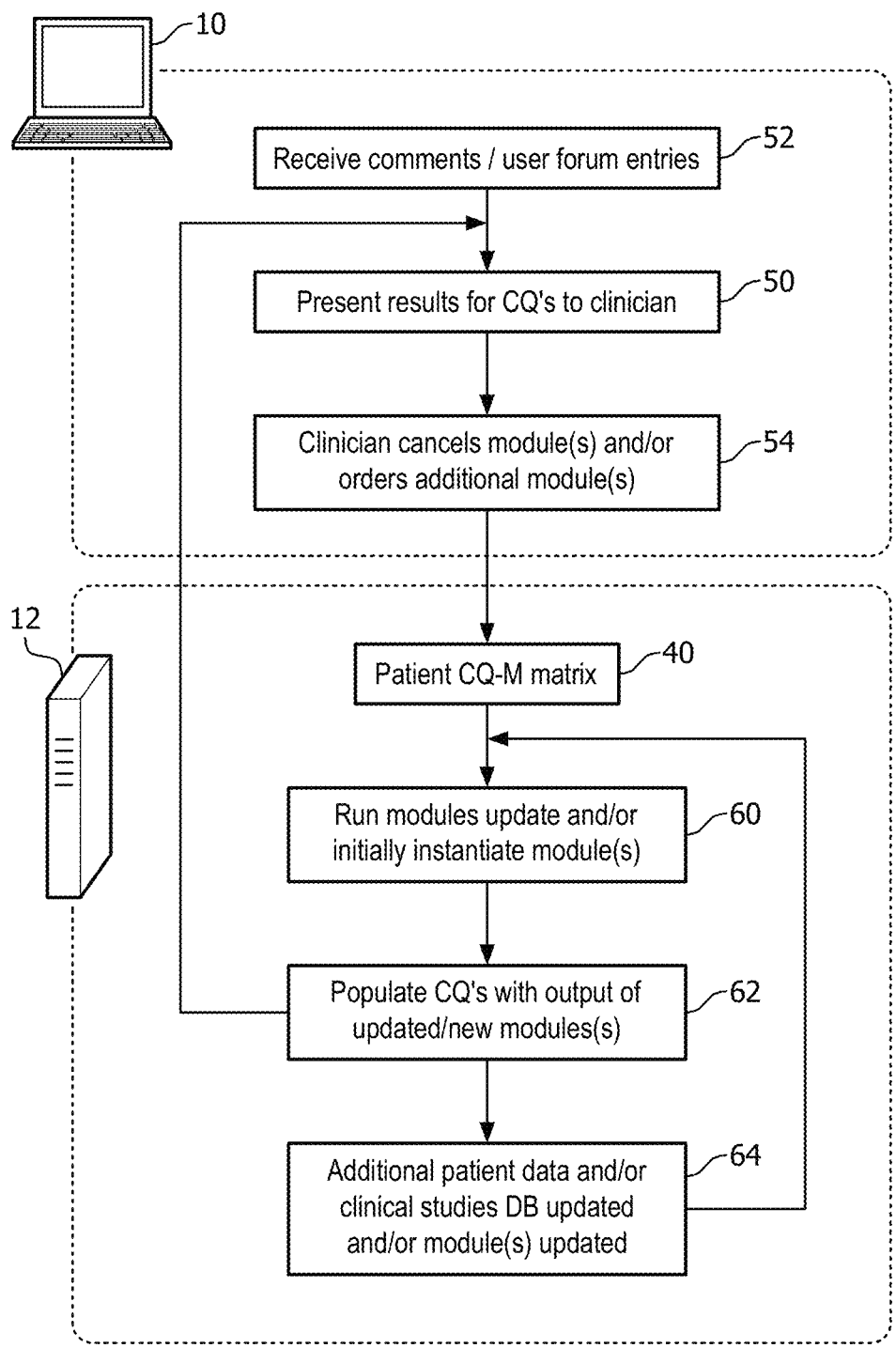

FIG. 7 diagrammatically shows clinician interaction with the clinical decision support system as disclosed herein including clinician selection of analytical modules.

FIGS. 8-16 diagrammatically show screenshots of a user interface for the clinical decision support system of FIGS. 6 and 7 suitably implemented on the user interfacing computer of FIG. 5.

The disclosed clinical decision support (CDS) systems are designed to provide a flexible framework for guiding diagnosis and treatment, while at the same time providing tools by which medical personnel can modify the workflow. The disclosed CDS systems provide the guidance of a workflow without limiting the flexibility of the diagnostic and treatment process to conform with the workflow. The disclosed CDS systems also leverage the availability of bulk molecular data (e.g. whole genome sequence data, standard microarray assays, or so forth) by reusing data where appropriate. Data analysis is arranged into reusable blocks, or modules, that are assembled in various ways to answer specific clinical questions. In this framework, a clinical question can be defined as a subset of analytical modules that jointly inform a clinical decision or action. By such arrangement, it is also assured that a data analysis modification in one part of the workflow is incorporated into all other parts of the diagnosis and treatment process that utilize that data analysis. The disclosed CDS systems also leverage the availability of bulk molecular data to pre-compute information likely to be useful to medical personnel, so as to reduce delays.

Disclosed embodiments comprise a software platform running on a hospital network server, Internet-based server, or so forth with which medical personnel interact via a personal computer, "dumb" terminal, or other computer running a web browser (although other hardware configurations are also contemplated). These clinical questions, modules and pipelines may reside over multiple computers over many geographic locations and the passing of the information should be preferably over a protected communication channel, involving encoded or compressed data. The elements of the system such as the CQ-M data structure and the modules and pipelines can be themselves encoded to provide security that is mandated for clinical use. The system enables a user interface/experience that delivers complex clinical information grouped and contextualized under an interrelating matrix of clinical questions and analytic modules. While a default clinical questions-analytic modules matrix is provided, this matrix can be personalized for each patient and for relevant patient groups and in accordance with any hospital-specific workflow guidelines so that the clinician is not locked into any specific workflow. In some embodiments, the front-end of the system also provides levels of authentication and authorization dependent on the user and patient information. Furthermore, the back-end components of the system provide access to patient data as well as to the analytic modules that contextualize the data for the current patient and current user (e.g. clinician). In addition, the back-end provides capability to selectively activate or deactivate analytic modules in variance of the default matrix to provide the clinician with precise control of the access, interpretation, and visualization of data. Execution of the analytic modules is in accord with data processing pipelines that are activated automatically by the default or patient-specific matrix or on-demand based on the patient data and the actions of the clinician.

Illustrative embodiments implement a method to manage complex patient data of multiple types in a clinically-consistent and actionable manner enabling effective and optimal clinical decisions relying on evidence-based medicine. The system employs elementary units of clinical questions pertinent for a particular stage of the healthcare cycle that correspond to actions including modules and pipelines. A module enables access or interpretation of an aspect of the patient data. The analytic module typically combines one or more sets of information around an output that provides a clinical component in the overall input. For example, an analytic module may perform an (in silico) diagnostic test. Pipelines provide the structure to acquire existing data, or generate new data based on existing patient data. A pipeline comprises a combination of steps that perform a sequence of operations, and has defined input parameters and a designated sequence of execution components (e.g. alignment, sorting, annotation, statistical evaluation) that complete the task performed by the pipeline. In other variant topologies, an analytical module may call for several pipelines to acquire input data, and/or a pipeline may provide input for two or more analytical modules. A generalized framework is suitably based on a clinical care cycle or workflow (e.g. screening, diagnosis, treatment, and monitoring in some oncological care cycles), such that each stage of the workflow has one or more hospital-prescribed clinical questions which may be answered by one or more analytical modules.

The disclosed clinical decision support systems employ clinical questions (CQ's) as an organizing framework. Clinical questions group modules and link pipelines to modules.

In some embodiments, the clinical decision support method includes associating computer-implemented analytical modules with clinical questions, computing outputs of computer-implemented analytical modules for a patient, and displaying information for the patient pertaining to a clinical question comprising outputs computed for the patient of the computer-implemented analytical modules associated with the clinical question.

With reference to FIG. 1, more formally, each patient context is represented with a number of clinical questions (denoted by boxes labeled "CQ" in FIG. 1). Each of these clinical questions in turn is represented with the data from one or more analytical modules (denoted "M" in FIG. 1). Data flow in FIG. 1 is represented by block arrows. Data are generated by combining the outputs from modules and pipelines (denoted "P" in FIG. 1). Pipelines comprise multiple data analysis steps of which (in general) some are individual tools (denoted "S" in FIG. 1) and some steps are other pipelines. In this topology, information is retrieved on demand, top-down starting from the clinical questions through modules to the pipelines. In every data retrieval request, if the data is available, then it is returned immediately, and if not, then the request is sent to the responsible module or pipeline which triggers the adequate steps that ultimately deliver the requested data.

With reference to FIGS. 2 and 3, as an example of the relationship between clinical questions, modules and pipelines, the use of the Gene Fusion module for therapy selection in breast cancer is described. In FIGS. 2 and 3, data flow is again represented by block arrows, and each entity is labeled by its name and is identified by a box appended in the upper-right as a clinical question (CQ), analytical module (M), pipeline (P), or step (S). The Gene Fusion module detects the presence of targetable gene fusions using patient RNAseq and DNAseq data. Some illustrative examples of targetable gene fusions in breast cancer include Mast Kinase and Notch gene family fusions that are likely targetable by γ-secretase inhibitors. This module will therefore be associated with the therapy selection clinical question in this context, as shown in FIG. 2.

As shown in FIG. 3, the Gene Fusion module suitably uses intermediate patient data produced by the RNAseq and/or DNAseq pipelines. The RNAseq pipeline can be used to identify gene fusion events with high confidence—steps such as deFuse, TopHat2 etc are examples of analysis tools that can detect the presence of gene fusion events in patient RNAseq data. Once a set of candidate fusions are called, the DNAseq pipeline can be used to confirm those fusions that may have resulted from genomic breakpoints associated with deletions, amplifications or translocations. Examples of steps used in pipelines or analysis tools that can identify genomic breakpoints events are BreakDancer, Pindel, SVMerge etc.

The Gene Fusion module identifies high confidence gene fusions in the patient tumor and then checks for known associations of said fusion events with clinical action in the clinical knowledge base. In cases where a known association with therapy response exists, the Gene Fusion Module passes the detected gene fusion and associated clinical association in the context of the therapy selection clinical question. This allows for clinicians to be presented with clinically-relevant gene fusions in the context of a given patient without having to perform any targeted discovery. Furthermore, the system enables a practicing oncologist to gain access to the most current gene fusion biomarkers with strong levels of evidence for clinical action without having to spend valuable time investigating literature or waiting for the biomarker to be included in treatment guidelines.

With reference to FIG. 4, in some embodiments, the clinical questions are described in terms of analytic modules (M) through a clinical question-module matrix (i.e. CQ-M matrix) shown diagrammatically in FIG. 4. The following notation is used without loss of generality: assume there are n modules, m pipelines, and k clinical questions, and j stages of the care cycle. One clinical question (e.g. prognosis) may be addressed with several modules (e.g. 21 gene signature, or 70 gene signature). Each module is enabled by one or more computational pipelines. A single pipeline can be used by several modules. In the representation of the CQ-M matrix shown in FIG. 4, the k matrix columns correspond to clinical questions (CQ1, CQ2, CQk) and the n rows correspond to analytic modules (M1, M2, Mn). Each cell of the CQ-M matrix that is marked with a filled circle marker corresponds to an entry in the clinical question of that column, which may be expressed in the following format:

Clinical question: $CC_i$
<Clinical question output>: a list of key-value pairs describing the outputs $CC_i$
Module: $M_j$
<Module output>: a list of key-value pairs describing the output and the value from $M_j$ For example, in a breast cancer clinical decision support system the clinical question "Prognosis" may be associated by the CQ-M matrix with the module "Molecular Subtypes" as per the following entries:

Clinical question: Prognosis
<Clinical question output>: {prognosis: good}
Module: Molecular Subtypes
<Module output>: {subtype: Luminal_A}

This is for a patient with Luminal A breast cancer having a good prognosis. In other patients, the values may be different (e.g., prognosis: poor, subtype: Basal, et cetera).

It will be appreciated that the CQ-M matrix can have variant representations. For example, the rows may represent the clinical questions and the columns the modules. Other data structures can be used to contain the relationships between the analytic modules and the clinical questions not necessarily similar to a matrix. For example, a graph representation with two types of nodes (CQ and M) and vertices symbolizing the link can also capture the CQ-M matrix content. In general, each stage of the care cycle may employ a different CQ-M matrix. For example, for breast cancer, for the screening stage, the CQ-M matrix will include clinical question predisposition, which may invoke modules for mutations on the BRCA1/BRCA2 genes. For the diagnosis stage the clinical questions may include a subtyping module.

The CQ-M matrix has numerous advantages. It facilitates re-use of data, since when an analytic module is included in two or more clinical questions the same module output can be used in answering those clinical questions. For example, in FIG. 4 the module $M_5$ is included in two clinical questions $CQ_1$, $CQ_3$. The output of analytical module $M_5$ is computed once, and the results can be used for both $CQ_1$, $CQ_3$. The CQ-M matrix also facilitates updating the clinical decision support system when new data become available. For example, if an updated genetic sequence is acquired for the patient and module $M_5$ is re-run on the updated genetic sequencing data, the updated $M_5$ output is automatically populated to clinical questions $CQ_1$, $CQ_3$. The CQ-M matrix also enhances flexibility since it is not constructed as a branching linear workflow. Rather, the clinician can move between clinical questions, and if updates are made to modules while analyzing one clinical question such updates are propagated to other clinical questions in accord with the entries of the CQ-M matrix.

At the same time, the processing pipelines can be constructed to constrain such flexibility where appropriate. For example, in a breast cancer clinical decision support system, execution of a clinical question directed to treatment may not be allowed until the clinician accepts (or designates) a diagnosis including cancer typing, staging, and estimation of the prognosis. A specific clinical workflow may pertinently involve multiple clinical questions in a designated order by the hospital guidelines or guidelines set by a regulatory entity.

The disclosed clinical decision support systems optionally leverage the availability of bulk molecular data (e.g. whole genome sequences, microarray data, et cetera) to pre-compute results for some modules. In one approach, the list of modules ($M_1, \ldots, M_n$) is defined for a disease or condition (e.g. breast cancer in the illustrative example) and upon establishing this disease or condition in a patient a pre-defined standard set of modules is executed. These modules are chosen for pre-computation based on the data available and/or the analysis pipelines implicated in computing the output for the modules. Once module data are computed, the module can be assigned to an appropriate category for a given clinical question, such as Actionable or Useable (informative). The definition of "Actionable" and "Useful" is specific to specific CDS system implementations, but in general an "Actionable" designation indicates that the module or other element has gone through a rigorous approval mechanism (e.g. at a national, regional, or hospital level), while the "Useful" designation indicates that the module or other element is believed to be informative but it is at present under investigation, or designated for research use only, or so forth. The priority and usefulness of an analytical module is optionally also linked to the other factors, such as the level of clinical evidence that is associated with the module, clinical guidelines of the particular healthcare institution making use of the clinical decision support system, preference based on a vendor or geographic location (speed of getting results), or so forth. A module that yields to some output can by default be categorized as Useable; while a module that yields some output that contributes to a clinical question with associated clinical evidence or Food and Drug Administration (FDA) approval, or American Society of Clinical Oncology (ASCO) clinical guideline recommendation, is categorized by default as Actionable. However, these are only default categorizations. The designation of the modules and their user interface representation is customizable, so that the clinician can override the default category of a module for a specific patient.

For example, a Gene Mutation module that returned one or more mutations that are not defined to directly contribute to one or more clinical questions (e.g. therapy selection, clinical trial selection) but may be used to further characterize a decision will automatically be categorized as Useable. However, the clinician can add this module to a clinical question "Clinical Trial" if for example a clinical trial is recruiting patients with a particular mutation and with this the module will be categorized as Actionable. On the other hand, if this module was categorized as Actionable due to a direct evidence for a therapy selection T, once the user makes a decision not to select therapy T (and if the module is not actively used in any other clinical questions), the module will be re-categorized as Useable.

For modules defined for the patient's condition that have no data computed, data processing/analysis pipelines are defined that can be executed automatically or manually triggered by the user. In one embodiment, pipelines are defined by a list of entries such as the following:

Pipeline name/descriptor processing module(s)

start conditions input parameters output parameters

In the pipeline, the steps may be organized to execute in a specific sequence if the execution of one step uses the output of another steps as input. A module may implement several statistical assessments (e.g. Wilcoxon test, principal component analysis) or machine learning algorithms (e.g. nearest neighbor clustering method). Some of the modules perform annotation function, e.g. assigning gene names or long noncoding RNA to a genomic location.

The input data can be mapped to the analytical module in various ways. In one approach, a designated data repository maps modules to pipelines. In another approach, this mapping is performed at the level of a clinical question, so that the description of a clinical question also includes corresponding pipelines for each of the modules in the clinical question. The output may be visualized a simple numerical value, descriptor, annotation, graph, heatmap or a pathway visualization.

Table 1 and Table 2 present illustrative generic pipeline and analytical module definitions, respectively. Table 3 presents an illustrative RNAseq pipeline definition, while Table 4 presents an illustrative Molecular Subtypes (PAM50) analytical module definition. In some embodiments, the output is formatted for user review via the Physician Analytics Application (PAPAyA), which is a software platform for genome informatics and decision support, and the delivery process step delivers the output to PAPAyA.

TABLE 1

Pipeline Definition

| Data | Process step(s) | Description |
| --- | --- | --- |
| | Instantiate pipeline (<parameters>) | The computational pipeline is initiated with certain parameters (e.g. patient ID, pointer to raw data source, sample ID, date of sample acquisition, pointer to annotation, versions of reference databases, etc) |
| Input data | | List data sources and dependencies (i.e. which data is output from other pipelines), any other conditions that need to be satisfied to claim the data is read for the next step. |
| | Start computation | List steps and conditions that need to be met for a step to move forward |
| Intermediate data | | List intermediate data and whether it is temporary or could be discarded after the pipeline completes |
| | End computation | |
| Output of pipeline | | Describe output data (format(s), pointer to data store, etc . . . ) |

TABLE 2

Analytical Module Definition

| Data | Process step(s) | Description |
|---|---|---|
| Input data | Invoke module (<parameters>) | The module is invoked with certain parameters (e.g. patient ID, sample ID, patient context, pointer to annotation, versions of reference databases, etc) List data sources and dependencies (i.e. which data is needed from which pipelines), any other conditions that need to be satisfied to run the module |
| Output data | Patient-specific module execution | Describe the module(s) that would use this data to produce output. How is the patient context used to query pipeline outputs and knowledge-bases to produce results Data that is generated that remains in patient record |
| Output to user interface | Delivery to patient record | The data that is passed to the user interface |
| Feedback data | User interaction | Data in patient record changed based on interaction with module data |

TABLE 3

RNAseq Pipeline Definition

| Data | Process step(s) | Description |
|---|---|---|
| Input data | Instantiate pipeline (<parameters>) | Patient ID Sample ID Sample Date Reference genome version number and date GTF file pointer (gene transfer file, or a formatted file that annotates the genomic regions of interest and their function) One or more One or more fastq files Reference genome (indexed fa . . . ) |
| Intermediate data | Start computation | Input quality control QC (compute or retrieve) Alignment (e.g. tophat, bwa or another DNAalignment tool) Quantification (e.g. cufflinks for transcriptome) Output QC (e.g. principal component analysis PCA, number of #0 fragments per kilobase of exon per million fragments mapped FPKM transcripts, . . . ) QC summary (keep) Run logs (keep) Temp files (discard) Alignment output (keep) |
| Output of pipeline | End computation | Quantified genes/transcripts list Output QC information |

TABLE 4

Molecular Subtypes (PAM50) Analytical Module Definition

| Data | Process step(s) | Description |
|---|---|---|
| Input data | Invoke module (<parameters>) | Patient ID Sample ID Sample Date RNAseq pipeline output dependency: Output QC passed |
| | Patient-specific module execution | A module that implements a subtype classifier |

TABLE 4-continued

Molecular Subtypes (PAM50) Analytical Module Definition

| Data | Process step(s) | Description |
|---|---|---|
| Output data | Delivery to patient record | Subtype assignment (add to patient record) Additional data (execution log) |
| Output to user interface | | Subtype information for the patient, one of the breast cancer subtypes: LA = Luminal A, LB = Luminal B, E = Errb2, B = basal subtype assignment (add to patient record) |
| Feedback data | User interaction | Display distance values to the centroid of each subtype in a graphical format |

By virtue of the use of the CQ-M matrix, the relation between clinical questions and modules is not static. The default CQ-M matrix is copied for each patient (that is, a CQ-M matrix instance is assigned for each patient) and serves as the base or default matrix. The clinician can dynamically mold the contributions of each module for each clinical question. Based on the user interaction, the patient copy of the base CQ-M matrix is updated and customized for each patient. To include additional modules in a clinical question, the corresponding cells of the CQ-M matrix instance copy are updated to reflect such a change. Similarly, removing a module corresponds to change of the information in certain cell(s) of the CQ-M matrix. Furthermore, changes in one clinical question may result changes in another. For example, a module can be added by the clinician to a clinical question that recommends therapy T. This module is manually introduced to the clinical question by the clinician, which changes its category from Useable to Actionable. Re-categorizing the module as Actionable may result in changes to another clinical question (e.g. prognosis). If the prognosis clinical question was already instantiated for the patient, it will be updated to reflect the re-categorization of the module as Actionable. Alternatively, the clinical question may be instantiated anew due to the changes in this module. Similarly, if a module is removed by the clinician from a clinical question and this causes re-categorization from Actionable to Useable, one or more additional clinical questions may be affected by that change.

The CQ-M matrix provides the mechanism for linking and re-using modules in such ways.

Although not illustrated, it is also contemplated to employ a module-module matrix (M-M matrix) or a similar data structure that captures relationships between modules, to provide module-module links so as to capture relations between the modules. Alternatively, module-module dependencies can be defined for each existing module-module-clinical question combination, as part of the clinical question description. When the data in two modules under a clinical question matches the define criteria, additional information may be provided to the clinician linking the two modules. Another approach is to use an integrated three-dimensional CQ-M-M data structure.

With reference to FIG. 5, an illustrative architecture for embodiments of the system disclosed herein is diagrammatically illustrated. In this illustrative architecture, the system is implemented as a web-based application where the client side (top of FIG. 5) is executed on a web browser running on a computer 10 (e.g. a desktop computer, a notebook computer, a tablet computer, a cellphone, or so forth) that renders web pages (or similarly encoded text that translates into an interactive graphical interface) resulting from the actions from the clinician and the state of the server. The presentation for the user is designed as a user interface/experience which is built around the clinical application of the system and presentation of patient data allowing the user to actively interact with the relevant information in the most optimal way. A server computer 12 (which may be implemented as a distributed network of servers, e.g. a cloud computing configuration) connects with the user-interfacing computer 10 via a hospital network, the Internet, a home WiFi network of the clinician (if working at home), various combinations thereof, or so forth. The server computer 12 executes a program implementing a web server generating the web pages and receiving user inputs from the computer 10, and receives requests and sends information to the browser accordingly. All content and module access is verified and validated through an authentication and authorization layer implemented on the server computer 12 (and optionally also via other mechanisms such as a hospital network firewall) which ensures that each user (clinician) gains secure access to data and functionality to which they are entitled while maintaining patient privacy in accord with applicable governmental regulations, hospital policies, and so forth. As diagrammatically shown in FIG. 5, the underlying clinical context and patient management functionality allows the clinician to navigate through patient records, view patient data and interact with the patient information structured around the analytical modules and clinical questions, organized in accord with the CQ-M matrix of FIG. 4.

In the architecture of FIG. 5, the modules may be implemented as plug-ins or other modular computing elements, and the server 12 maintains a list of installed computer-implemented analytical modules each defined with a number of attributes such as module name, input parameters, output parameters, source and/or executable code, required libraries, and so forth. Pipelines are similarly defined as a list of entries as previously described. The system components operating under the web server access one or more databases included with or accessibly by the server computer 12. For example, the databases suitably contain patient data, and also metadata such as definitional entries for the modules, clinical questions, and pipelines, and optionally other system data such as records of current and past user sessions, activity logs, and so forth.

These databases may also include social media aspects. For example, a public comments section or users forum may be included for each module and for each clinical question, in which clinicians can provide information of general interest, such as a description (or warning) of a software bug in a module identified by a clinician, comments on ways clinical information generated by a module may be used in patient diagnosis and/or monitoring, or so forth. Comments in the public comments section or public forum are suitably processed to maintain anonymity, using automated processing (e.g. an algorithm to detect and remove personal names) and/or moderation of the comments section or forum by system administrators (e.g., a comment must be reviewed by an administrator before it is visible to other users). The level of public access may also be controlled, e.g. comments may be visible to all users, or only to users with a certain (minimum) access level. Such a public comments section or public user forum may also include a ratings system by which users can rate modules (optionally including the ability to input comments explaining the choice of rating), so that clinicians can readily determine how reliable other users consider a given module. These public comments, forum entries, and/or ratings are also expected to be useful to system administrators for purposes such as detecting software bugs, identifying unclear user interfacing dialog components, receiving user requests for new analytical modules, or so forth.

The databases may also include a private comments section or private forum for each patient, access to which is limited to the patient's physician and other medical personnel authorized to access the patient's information. Such mechanisms facilitate communication between the patient's physician and various medical specialists that may also be treating the patient. Thus, for example, if the pulmonary specialist prescribes a new medication for the patient, he or she can add a comment to ensure the primary care physician and any other treating specialists are aware of the new medication. Moreover, since the pulmonary specialist is most likely to be aware of factors such as common side-effects of the new medication, the pulmonary specialist can identify any such factors in the comment identifying the new prescription.

Illustrative FIG. 5 employs a browser-based user interfacing architecture. This architecture advantageously leverages user interfacing capacity built into the web browser typically loaded onto most desktop computers, notebook computers, tablet computers, and so forth. The web browser may, for example, be Firefox™ (available from Mozilla.org, Mountain View, Calif., USA), Chrome™ (available from Google Inc., Mountain View, Calif., USA), Internet Explorer™ (available from Microsoft Corp., Redmond, Wash., USA), Safari (available from Apple Corp., Cupertino, Calif., USA), or so forth. However, other configurations are contemplated. For example, a dedicated user interfacing program can be loaded onto each user interfacing computer 10, which is then run when the clinician wishes to access the clinical decision support system using that computer 10. It is also contemplated to shift processing from the server 12 to the user-interfacing computer 12. For example, if the processing capacity of the computer 10 is sufficient, some or all of the modules may be downloaded to and execute on the user interfacing computer. Such a variant provides distributed computing capability leveraging the user interfacing computers. In such embodiments, the output of the module is preferably uploaded back to the server computer so that it can be re-used in other clinical questions.

It will also be appreciated that the clinical decision support system functionality performed by the combination of the user interfacing computer 10 and the server computer 12 can be embodied as a non-transitory storage medium storing instructions executable by the computers 10, 12 to perform the clinical decision support operations disclosed herein. The non-transitory storage medium may, for example, comprise a hard drive, magnetic disk or other magnetic storage medium, and/or an optical disk or other optical storage medium, and/or random access memory (RAM), read-only memory (ROM), flash memory or other electronic storage medium, or a combination of distributed networked storage drives accessible in a cloud-like infrastructure or so forth.

With reference to FIG. 6, operation of the clinical decision support system of FIG. 5 during initial patient diagnosis and assessment is diagrammatically shown for the illustrative case of a breast cancer patient. An initial patient diagnosis 20 (of breast cancer, in this example) is made by the physician based on physical examination of the patient, patient history and described symptoms, and any other information available to the physician. A biopsy 22 is ordered and performed to extract a sample of the breast tumor (and, optionally also of healthy tissue for comparative purposes), and the biopsy sample(s) are processed by a histopathology laboratory 24 and a DNA sequencing laboratory 26. In parallel, the patient may optionally undergo imaging 28, for example using one or more of magnetic resonance imaging (MRI), computed tomography (CT) imaging, positron emission tomography (PET) imaging, single-photon emission computed tomography (SPECT) imaging, ultrasound imaging, or so forth. Based on the biopsy, molecular data, and optional imaging information, the physician confirms the diagnosis of breast cancer in an operation 30 and may optionally make an initial assessment of the cancer type and stage at this point. This information is input to the clinical decision support system to create the patient record 32 (or update the record, if the patient is an existing patient receiving a new diagnosis of breast cancer).

It should be noted that in diagrammatic FIG. 6, dashed boxes are used to associate operations performed by the server computer 12 or by the user interfacing computer 10. However, it is to be understood that the computers 10, 12 operate together to embody the clinical decision support system, so that these designations are approximate. For example, the patient record creation/update operation 32 typically involves interaction between user inputs provided by the clinician via the user interface 10 and processing operations performed by the server computer 12. It will also be appreciated that the patient record setup may be performed in whole or in part by patient admissions personnel interacting with the server computer 12 via a third computer, not shown, e.g. a desktop computer disposed in the patient admissions office.

With continuing reference to FIG. 6, upon creation (or update) of the patient record, the server 12 performs an operation 38 to determine the clinical questions relevant to the patient based on the patient record including the initial diagnosis. The determination of the relevant clinical questions may, for example, be based on the clinical workflows prescribed by the hospital guideline for each part of the care cycle. Based on a defined workflow, one or more clinical questions are prescribed. The server also makes a copy 40 of the default CQ-M matrix 42 for the patient's diagnosis. In an operation 44, the server 12 runs those computer-implemented analytical modules identified from the patient CQ-M matrix 40 as being relevant to the patient and for which the requisite input data are available. This provides pre-computation of module outputs where possible (based on the available data) and likely to be helpful (based on the current patient record). In particular, the operation 44 typically pre-computes molecular data results for genetic tests that are likely to be probative (i.e. Useful or Actionable) for the patient given the initial diagnosis. In an operation 46, the results are presented to the clinician for review and manipulation by the clinician. It should be noted that there may be some delay between completion of the operation 44 and review of the results by the clinician in operation 46. On the other hand, if the clinician performs the review 46 before module processing 44 is completed, results for in-progress modules are indicated by appropriate annotation in the operation 46. It is also to be appreciated that the operation 46 may be performed more than once, by more than one clinician, e.g. by the primary physician and by one or more treating specialists.

With reference to FIG. 7, interaction with the clinical decision support system by the clinician after the initial setup of FIG. 6 is described. Again, dashed boxes approximately delineate operations performed by the server 12 and clinician-interfacing computer 10; again, these delineations are only approximate. In an operation 50, the current results (e.g. patient data, or clinical question results) for the patient are presented to the clinician Immediately after the patient setup (FIG. 6), the operation 50 corresponds to the initial results presentation 46 shown in FIG. 6.

At any time, the clinician can input comments to the comments section, user forum, rating system, or other "social media" component via the user interfacing computer 10, and these results are received in an operation 52. At the same time, other clinicians may input such commentary at any time. For example, the operation 50 may be currently being performed by the primary physician; while, at the same time, the pulmonary specialist may also be viewing the results (that is, a second instance of operation 50 may be being executed for the pulmonary specialist), and the pulmonary specialist may provide the commentary via operation 52. In either case (whether the commentary is provided by the primary physician or the pulmonary specialist in this example), the operation 50 is updated to display the added commentary.

The clinician can also interact with the clinical decision support system in an operation 54 by ordering one or more additional analytical modules to be run, and/or by canceling one or more analytical modules that have already been run.

As an example of the former, consider a genetic test that is not part of the ASCO clinical guideline recommendation for the patient's cancer—but the clinician is aware that recently published medical literature indicates that this test may be relevant. If the system administration has loaded a computer-implemented analytical module for performing this test, then the clinician can order this test be run. If the patient's whole genome sequence has been acquired, then this module can run using the available whole genome sequence to perform the genetic test in silico (that is, using stored genetic data, e.g. genetic sequencing or microarray data).

As an example of the latter, the clinician may be of the opinion that a genetic test that is part of the ASCO clinical guideline is not probative for this patient's case. But, because it is part of the ASCO guideline, the test is deemed Actionable and was pre-computed in the initial setup operation 44 (see FIG. 6). In this case, the clinician suitably chooses to either remove the (already-run) analytical module from the clinical question(s) considered or by accepting/ configuring clinical questions with alternative course of action, virtually remove the module from consideration. Modules that are removed (or canceled) still produce output, but a removed module is taken out of consideration in evaluating the clinical question. This can be done explicitly, e.g. a module is manually transferred from Actionable to Useful, or by accepting an alternative clinical question as a course of action which eliminates the clinical question for which the module is Actionable.

It is also contemplated for the clinician interaction operation 54 to include the ability to modify operation or characteristics of an already-run analytical module. For example, the clinician may choose not to cancel the ACSO guideline-recommended module, but rather to change its category from Actionable to Useful. As another illustrative modification, if two or more data sets are available for input to the module (e.g., equivalent genetic information available from a microarray and from a gene sequence), the clinician may choose which data set should be used as input to the module. Conversely, the clinician may re-categorize as Actionable a module that was originally categorized only as Useful if the clinician is aware of a clinical study for which the patient is eligible based on the output of the module.

With continuing reference to FIG. 7, after selection in operation 54 of one or more analytical modules to order, modify, or to cancel, this request is conveyed from the user interfacing computer 10 to the server computer 12 and the server computer 12. Where modules are added or removed from consideration (e.g. converted from Actionable to Useful), the server 12 updates the patient CQ-M matrix 40 to reflect the addition of the newly ordered module(s) and/or the removal of the previously run module(s). Where a module is re-categorized or otherwise modified, the server 12 updates the module description and/or categorization accordingly. In an operation 60, the server computer 12 runs module updates for any modules whose output needs to be updated based on modification made by the clinician in operation 54, and instantiates any new modules ordered by the clinician in the operation 54. In an operation 62, the server 12 populates the clinical questions with the updated (including canceled) or newly ordered modules. Note that the operation 60 runs each computer-implemented analytical module only once; but the results of running that module are populated to all clinical questions utilizing that module in the operation 62. The updated results are then conveyed to the clinician by repetition of operation 50. Advantageously, these updates are also conveyed to any other clinicians reviewing the patient via the system (e.g., the pulmonary specialist in the previous example). Moreover, the clinician who performed the modification(s) 54 can utilize the comments section or user forum to provide commentary received in an instance of the operation 52 so as to communicate the rationale for the modification(s) to other clinicians involved with treating the patient.

With continuing reference to FIG. 7, other changes may occur that are not instigated by a clinician via an instance of the operation 54, but which nonetheless may impact the results generated for the patient by the clinical decision support system. For example, system administrators may add a new analytical module to the system that is relevant to the patient (e.g., designated by default as Actionable or Useful for the patient's diagnosis). Additional patient data may become available, e.g. a new genetic sequence or microarray result, or new patient medical images acquired by MRI, CT, PET, SPECT, ultrasound, or so forth. When such changes 64 are received, the server 12 determines whether the output of any analytical modules should be instantiated, updated, or canceled based on these changes 64; if so, the server 12 performs an instance of the operations 60, 62 to instantiate or update the modules and the populating of their output to the clinical questions, and performs an update instance of the presentation operation 50 (if the clinician is online at the time of the update) to inform the clinician of the changes. Optionally, commentary is added to the comments section or user forum to inform clinicians treating the patient of the changes or updates. Such commentary can be added manually, e.g. by system administrators, or automatically, e.g. whenever a new patient dataset is received an automatic comment can be generated and added to the comments section.

In some embodiments, the changes 64 may include updates to knowledge bases utilized by the clinical decision support system. For example, the system may mine the web site clinicaltrial.gov to identify new clinical trials which are scheduled or taking place. When such mining identifies a new clinical trial for which the patient is a candidate, the system performs an update such as re-categorizing a module whose output indicates eligibility of the patient for the new clinical trial as Actionable, and/or adds commentary to the (patient-specific) comments section or user forum to inform clinicians of the new clinical trial and of the patient's eligibility for it. The complete user interaction and the steps the system enacted are stored and can be used both as an audit trail and means to generate complete clinical reports, and as a teaching or knowledge transfer tool that can be used to apply the same interaction sequence to similar patients. Such an audit trail can also be used as a means to assess, track and improve quality of patient management at the hospital level. Hospitals are increasingly focusing on implementing institutional level standardized treatment procedures, for example, the American Society of Clinical Oncology Quality Oncology Practice Initiative (ASCO QOPI) is looking to develop cross-institutional standards. Capturing the user interaction audit trail and aggregating it over all of the physicians within an institution will enable such quality assessment initiatives. In another variant, the audit trail is used to generate a new pipeline for performing the audit sequence of user interactions. This new pipeline can then be applied to other, similar patients, or used in a simulator mode for training new users.

Figure 8:
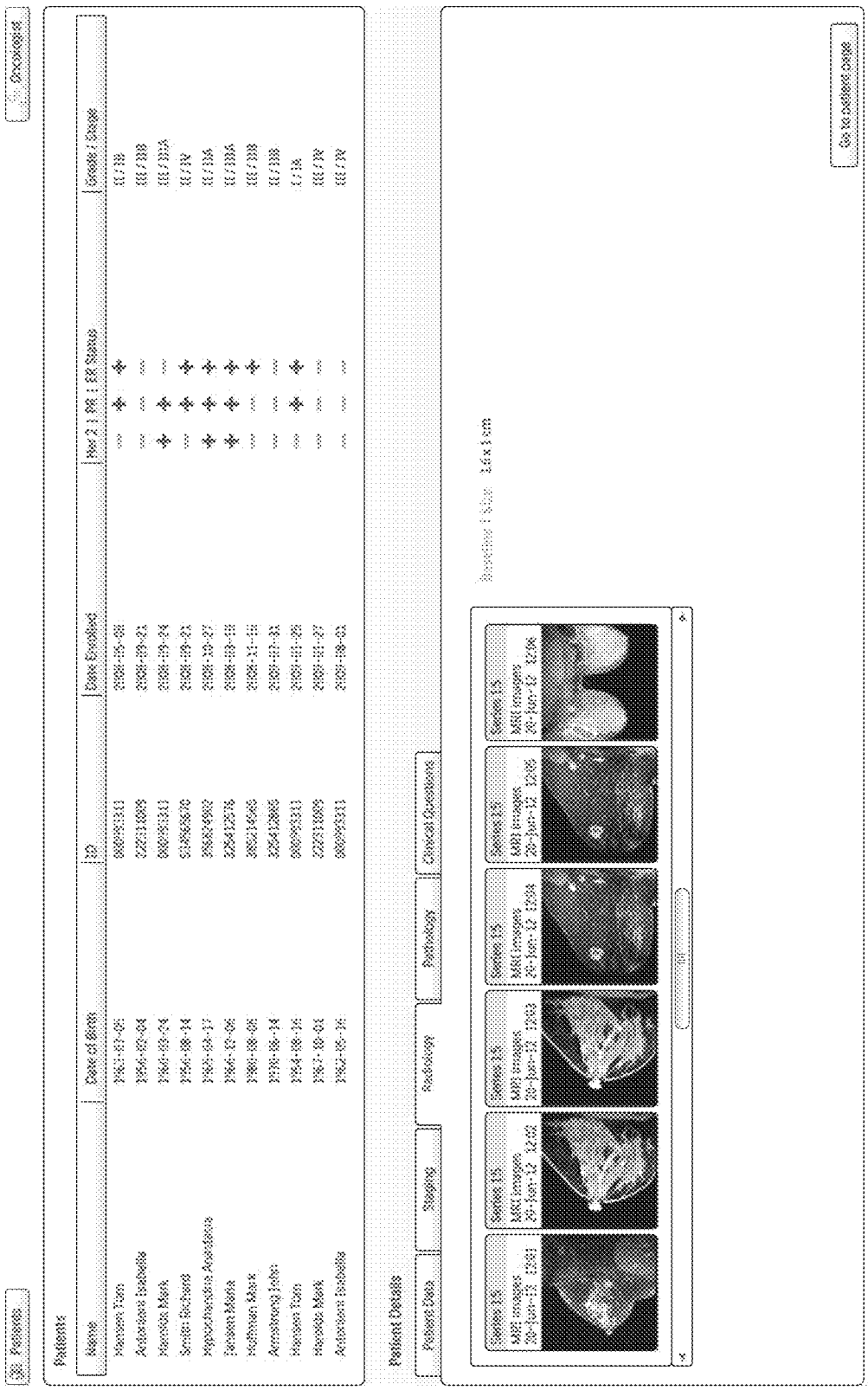

Starting with reference to FIG. 8, some illustrative user interface screenshots shown by the user interfacing computer 12 are described. FIG. 8 shows a patient list view in which one patient, "Antonioni Isabella" is selected. The lower half of this illustrative user interface screen includes tabs for various patient details, including: "Patient Data", "Staging", "Radiology", "Pathology", and "Clinical Questions". FIG. 8 shows the tab "Radiology" selected, and the lower half of the screen shows a series of MRI images for the patient.

Figure 9:
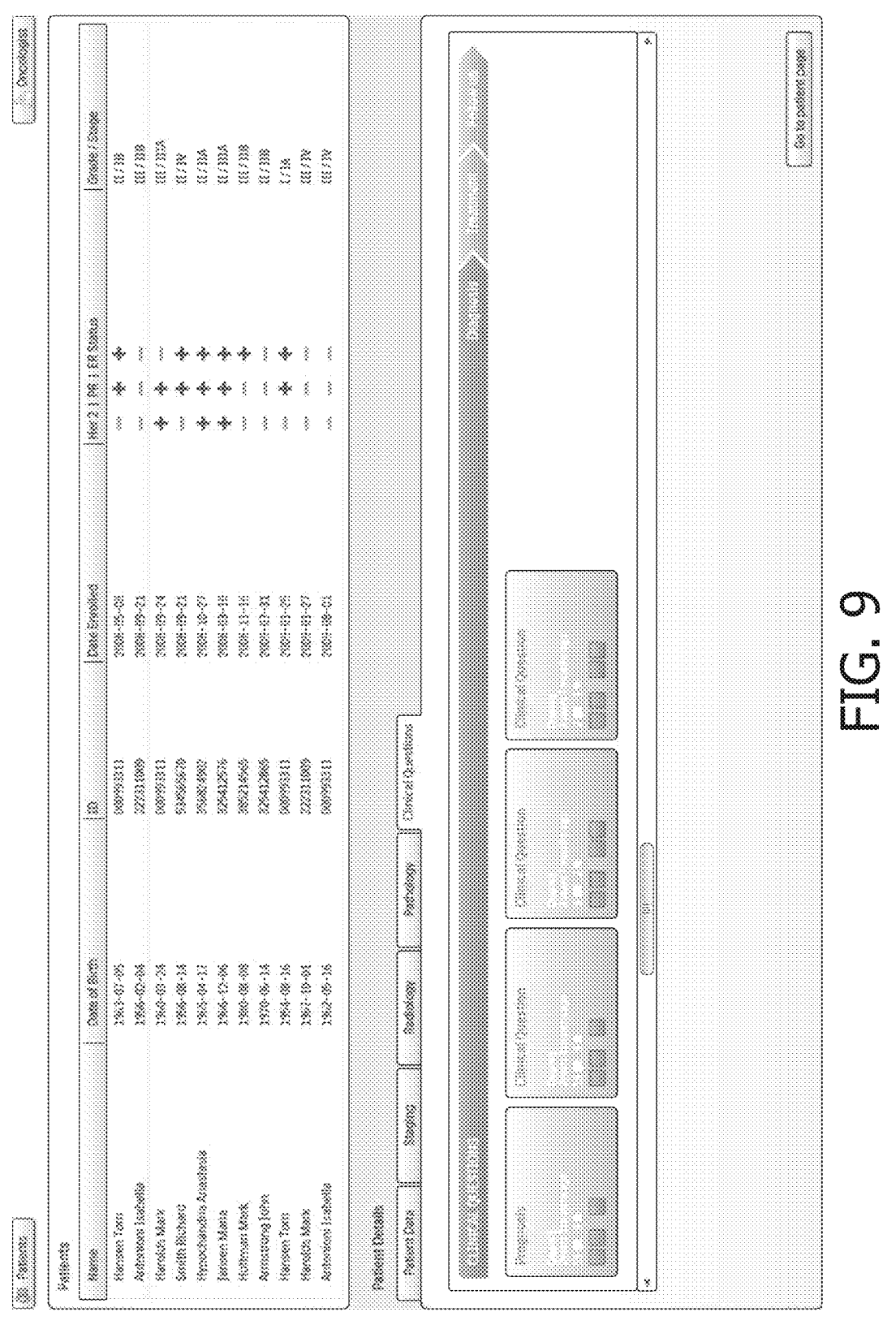

FIG. 9 shows selection of the "Clinical Questions" tab. This brings up a list of clinical questions in the lower half of the screen, including a highlighted "Prognosis" clinical question. The "Clinical Questions" display also includes sub-tabs for "Diagnosis", "Treatment", and "Followup". These sub-tabs provide high-level workflow constraints to the use of the clinical decision support system, in that a prognosis must be selected in the "Prognosis" clinical question under the "Diagnosis" sub-tab before the clinician can move on to the "Treatment" sub-tab, and similarly a treatment must be selected under the "Treatment" sub-tab before moving on to the "Followup" sub-tab. In other embodiments additional or other constraints may be similarly imposed—for example, in some embodiments a clinical question directed to treatment outcome may need to be completed before the system allows the clinician to move on to the "Followup" sub-tab. It will be appreciated that such high-level constraints provide the clinician with substantial freedom to explore the investigatory space as compared with a clinical decision support system that is based on a clinical workflow.

Figure 10:
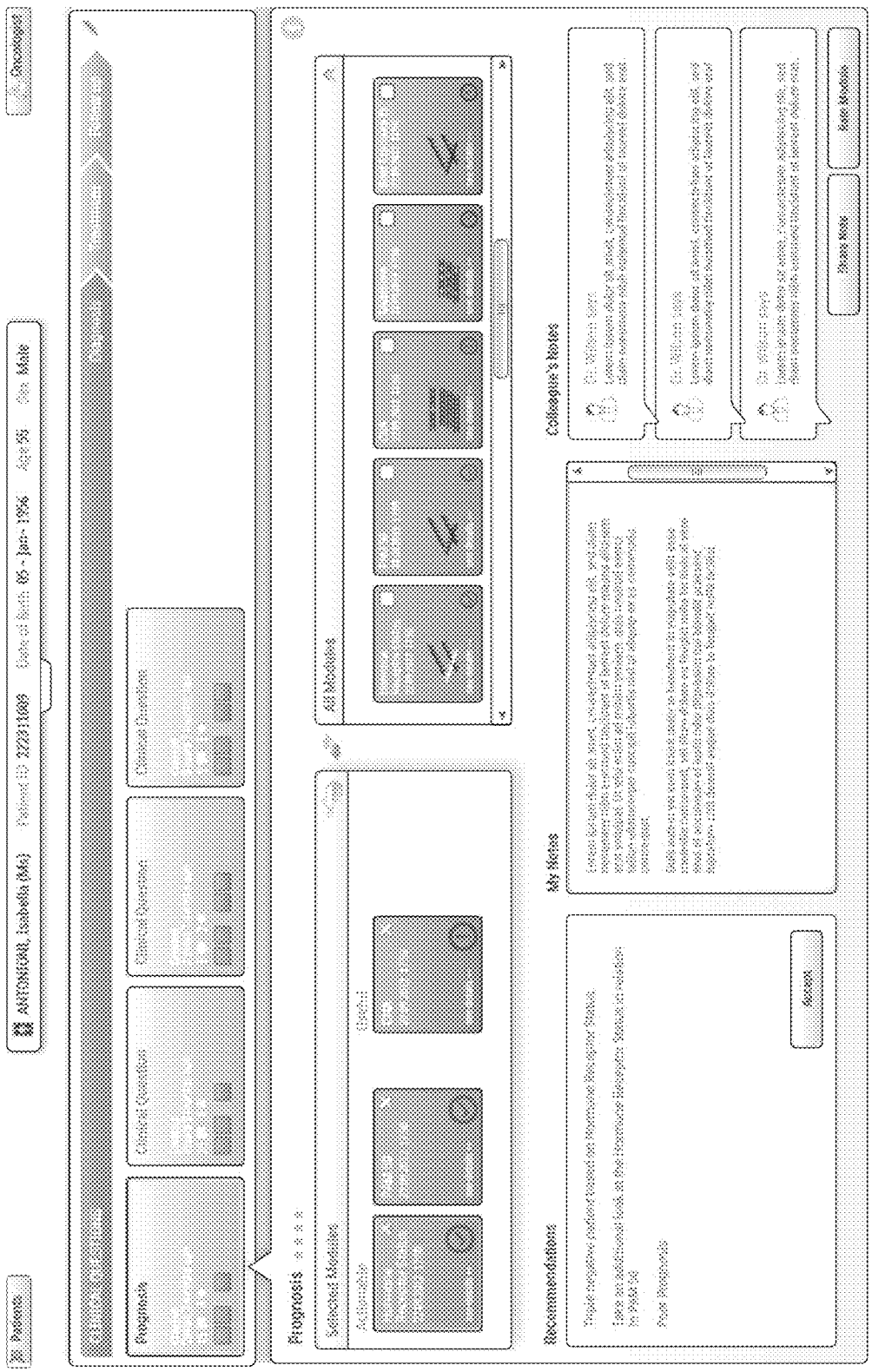

FIG. 10 shows a screenshot under the "Clinical Questions" tab with the "Prognosis" module selected and the module "Hormone Receptor Status" selected. The lower half of the window includes a leftmost "Recommendations" sub-window displaying recommendations based on the hormone receptor status determined by the hormone receptor status module. This sub-window includes an "Accept" button by which the clinician can accept the prognosis and recommendations and thus move on to the "Treatment" sub-tab. A middle "My Notes" sub-window displays the viewing clinician's notes, while a rightmost "Colleague's Notes" sub-window displays a comments section (private to the patient) listing comments of other clinicians having authorized access to the patient's data. User interfacing buttons "Share Note" and "Rate Module" shown below the "Colleague's Notes" sub-window enable the clinician to add commentary or rate the current module, respectively. The display also shows a "Selected Modules" sub-window listing the Active and Useful modules under the "Prognosis" clinical question (that is, the modules whose intersection with the "Prognosis" clinical question are marked in the CQ-M matrix of FIG. 4). These include the "Hormone Receptor Status" module categorized as Actionable, a "PAM 50" module categorized as Actionable, and a "CNA" (copy number alterations that describe gene copy number) module categorized as Useful. An "All Modules" window lists all modules operative for the patient. Not shown in FIG. 10 are other options, such as a user control to select a sub-window displaying the detailed output of the "Hormone Receptor Status" module (either replacing the "Recommendations" sub-window or displayed as a new window). Various other user interfacing controls and options are also contemplated, such as enabling display of output of two or more modules simultaneously, in a summarized format.

Figure 11:
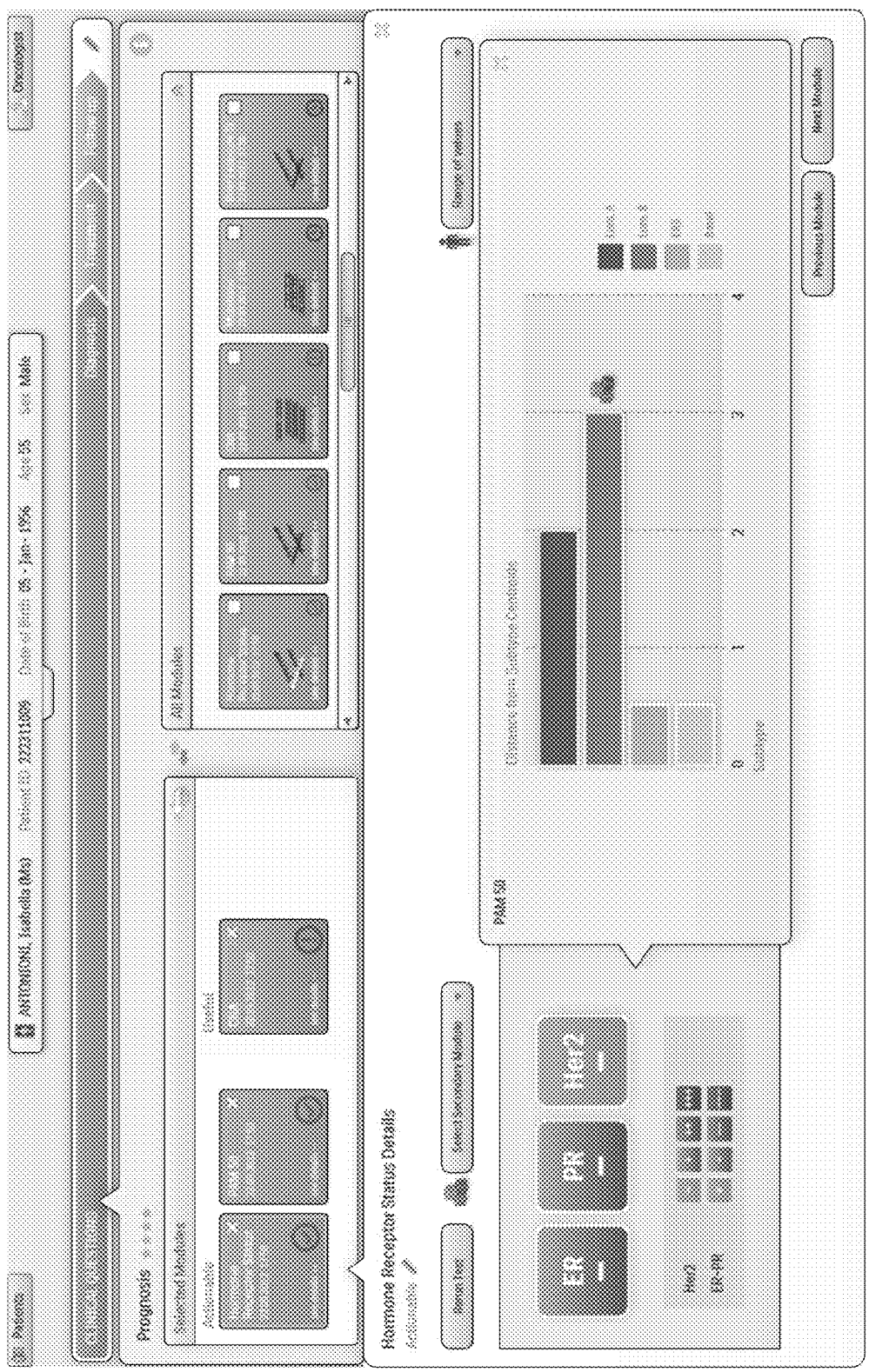

FIG. 11 shows selection of the "Hormone Receptor Status" analytical module as the primary module, and has selected the breast cancer molecular subtype "PAM 50" module (corresponding to Table 4) as a secondary module displayed as a pop-up window in the bottom right of the screen. The PAM 50 pop-up window plots distance from subtype centroids for the Lum A, Lum B, ERBB2, and basal breast cancer sub-types for the PAM 50 clinical molecular marker test as determined by the "PAM 50" module. Thus, the user can readily identify the breast cancer sub-type indicated by the PAM 50 classifier, and can compare this with the output of the "Hormone Receptor Status" module in assessing the "Prognosis" clinical question.

Figure 12:
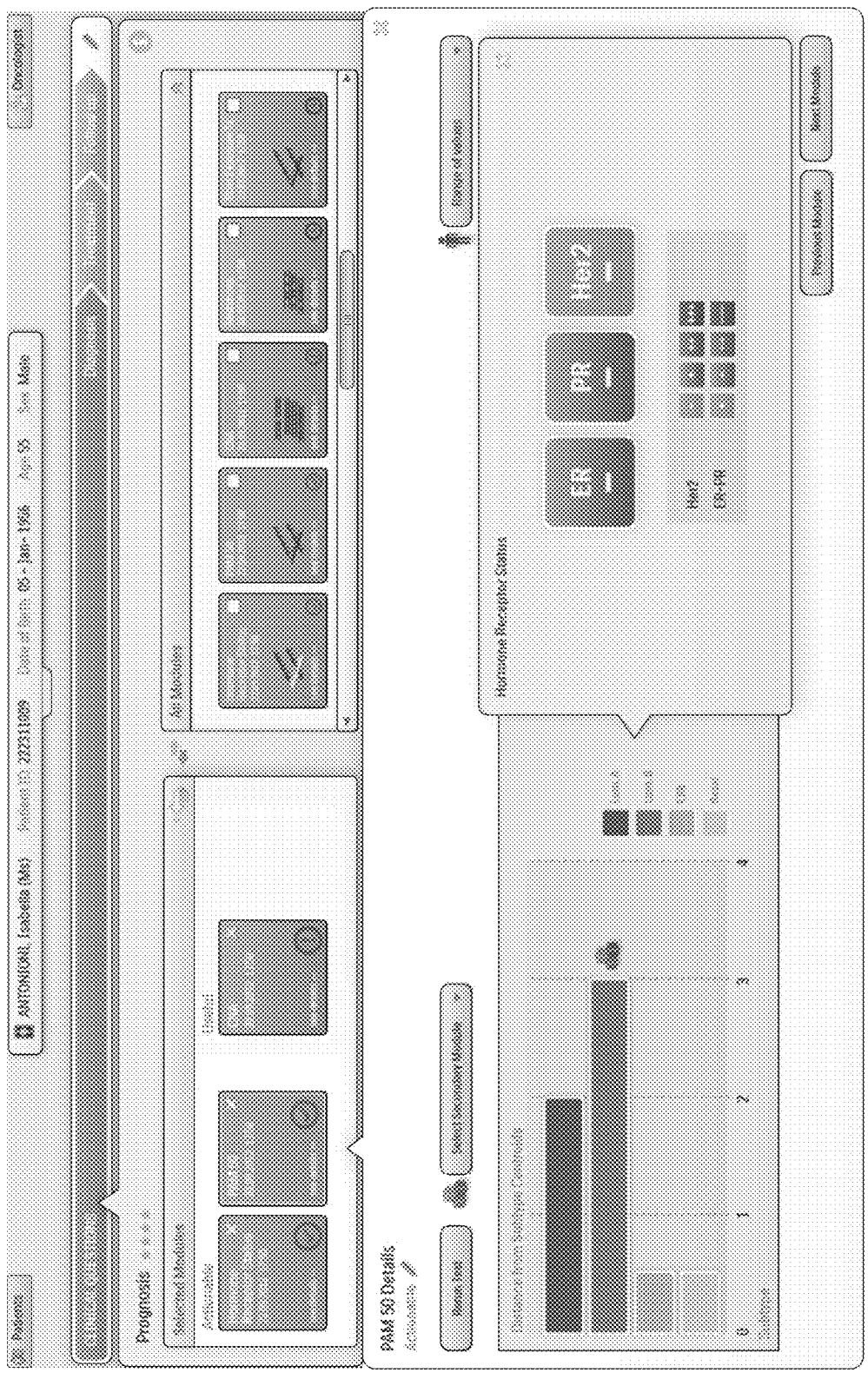

FIG. 12 shows an alternative user interfacing sequence, in which the user opened the "PAM 50" module as the primary module, and then brought up the "Hormone Receptor Status" module in a pop-up window. The same information content is displayed as in FIG. 11, albeit in swapped windows.

Figure 13:
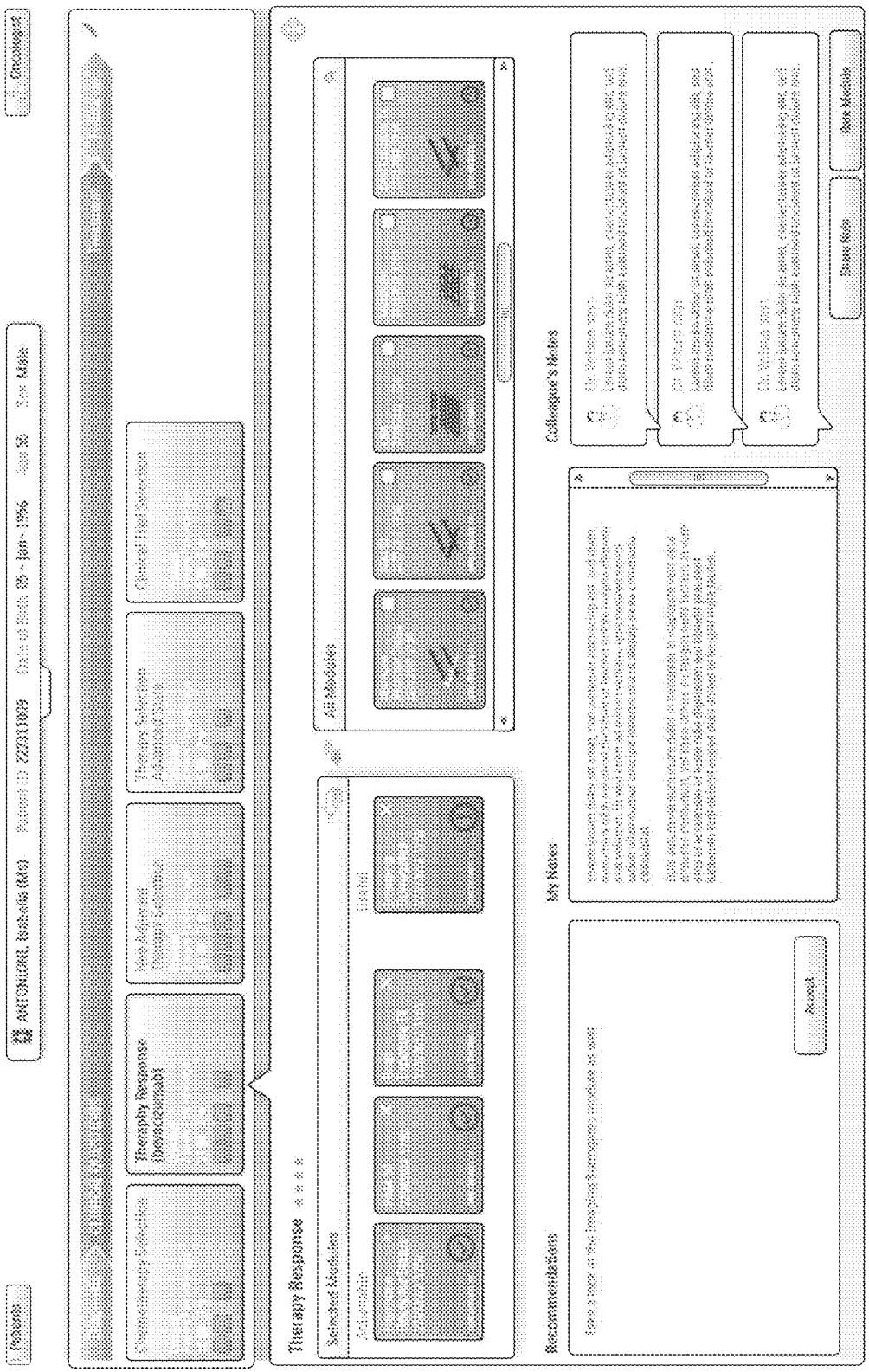

FIG. 13 shows a screenshot taken after accepting the prognosis and recommendation (that is, after selecting the "Accept" button in the "Recommendations" sub-window of the screenshot of FIG. 10), moving on to the "Treatment" sub-tab, and selecting a "Therapy Response" clinical question under the "Treatment" sub-tab. The lower half of the display provides a "Selected Modules" list of the modules associated by the CQ-M matrix with the "Therapy Response" clinical question. It will be noticed that the "Hormone Receptor Status" module and the "PAM 50" module are associated with both the "Prognosis" clinical question (see FIG. 10) and with the "Therapy Response" clinical question (see FIG. 13). However, a "Brief Exposure TX" module is associated with the "Therapy Response" clinical question (see FIG. 13) but not with the "Prognosis" clinical question. The lower half of the screen shown in FIG. 13 again includes middle "My Notes" and rightmost "Colleague's Notes" sub-windows.

Figure 14:
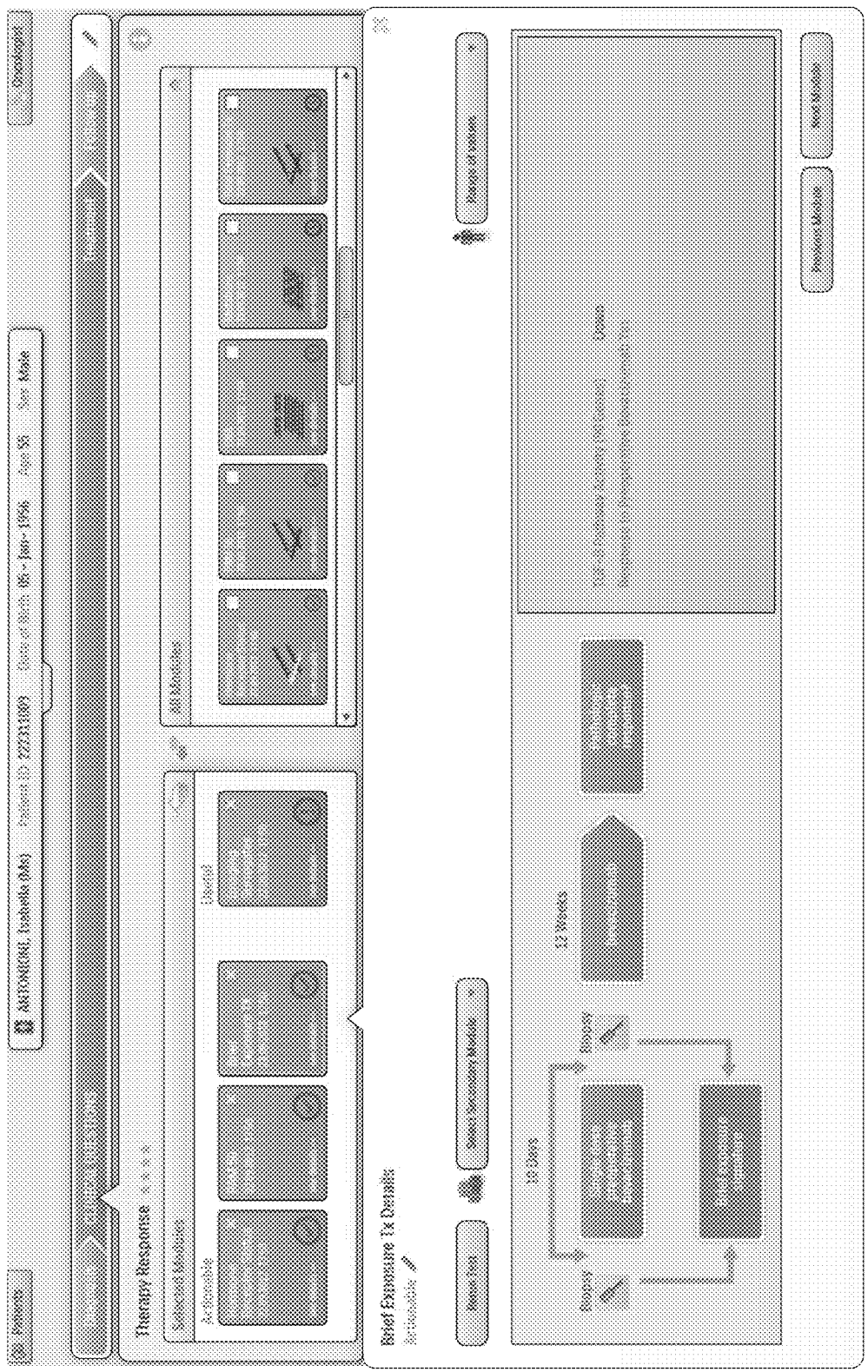

FIG. 14 shows selection of the "Brief Exposure TX" module, which brings up a diagrammatic representation of the therapy sequence, which includes an initial biopsy, a single dose of pre-operative bevacizumab, followed by a second biopsy ten days later. The results obtained for these two biopsies are compared in a brief exposure signature molecular test to determine the likelihood of a pathologic complete response (PCR) by the patient to the complete therapy. The sub-window to the right of the diagrammatic representation summarizes the interpretation of the brief exposure signature molecular test, which this patient shows a reduction in TGF-β pathway activity based on a 90-gene molecular signature test, which indicates a good likelihood of PCR for this patient in response to the full therapy sequence.

Figure 15:
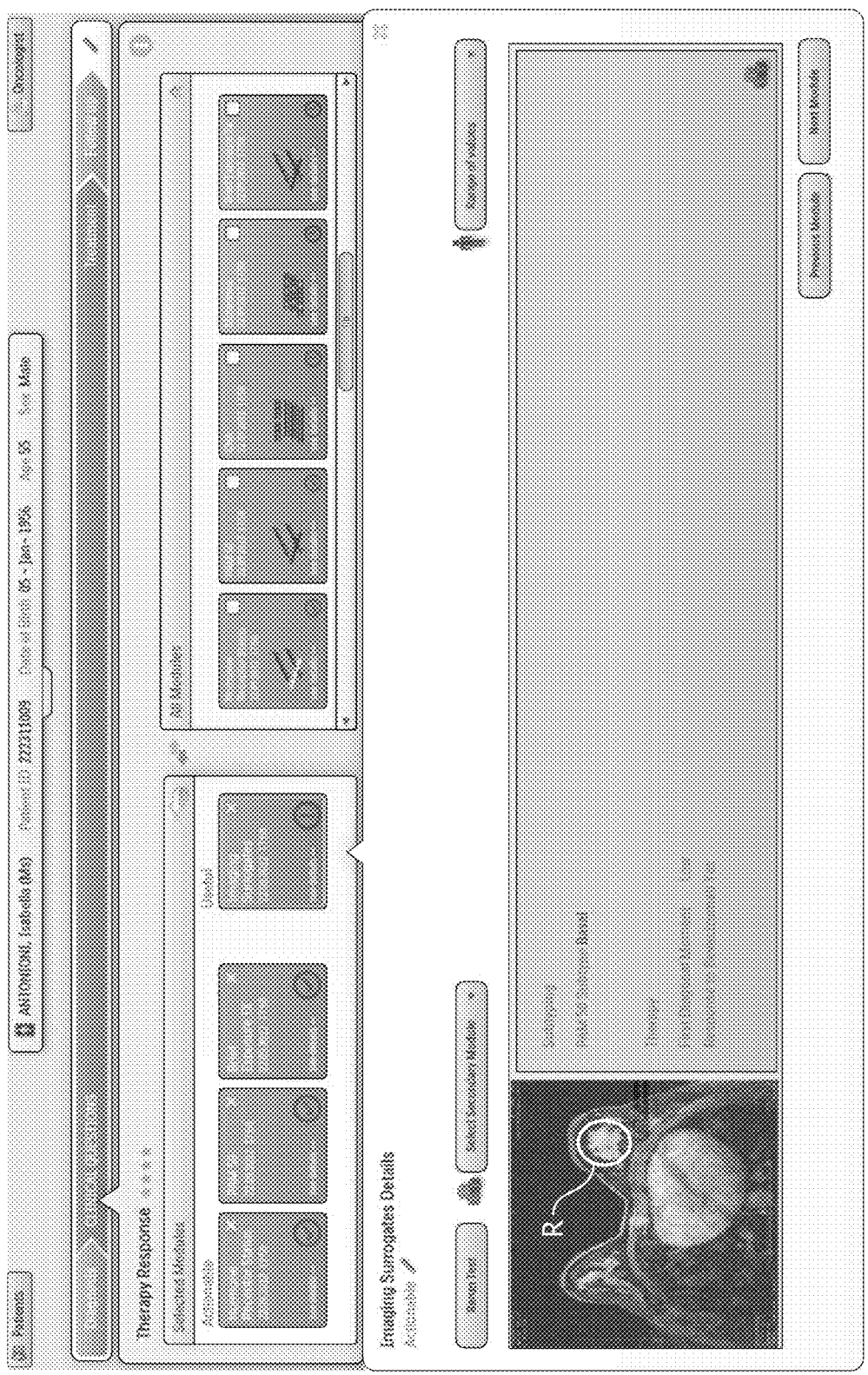

FIG. 15 shows selection of the "Imaging surrogates" analytical module, which is categorized as Useful, but not Actionable (in this instance). This module performs an analysis of the image texture in a region R of the right breast highlighted in the depicted clinical image. The analysis indicates that the image texture in region R (represented by several texture features such as contrast, correlation, angular second moment, entropy, etc.) correlates with the basal breast cancer sub-type as indicated by a PAM 50 molecular test. It will be seen that this is consistent with the result of the actual PAM 50 molecular test performed by the "PAM 50" module (compare with FIG. 11 or FIG. 12; this is consistent with the imaging test being a "surrogate" for the PAM 50 molecular test), but resolves an ambiguity in that the actual PAM 50 molecular test indicated similar distance from both the ERB and basal centroids.

Figure 16:
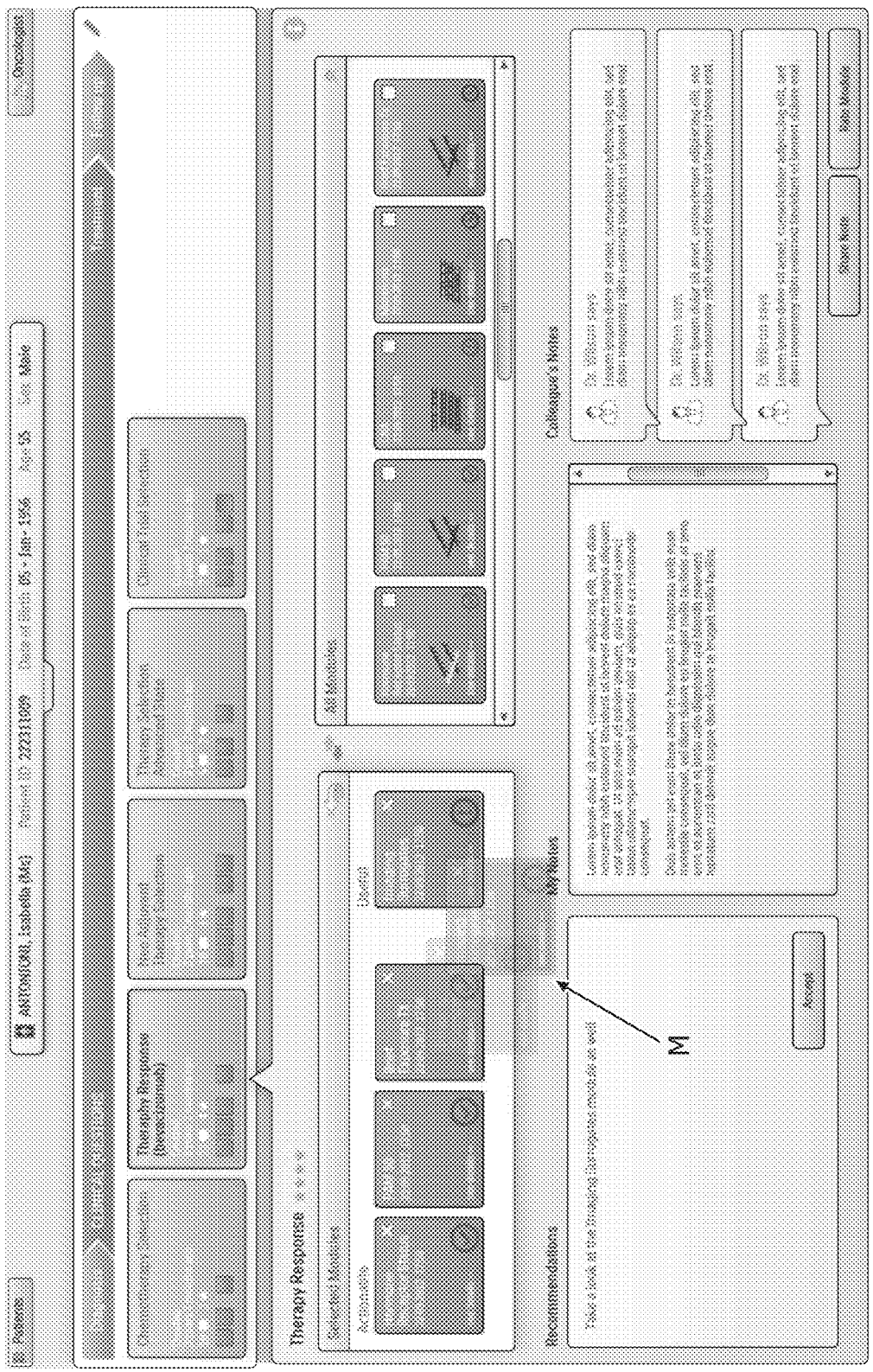

With reference to FIG. 16, the user concludes that the surrogate image test (FIG. 15) is of special value in view of resolving this ambiguity, and elects to move the icon representing the "Imaging surrogates" module from the Useful category to the Actionable category. This is diagrammatically shown in FIG. 16 by showing a sequence M of positions of the "Imaging surrogates" module icon as it is moved.

In one suitable user interfacing embodiment, the "Selected Modules" and "All Modules" sub-windows shown in FIGS. 10 and 13 are used to enable the clinician to order a new module or cancel an existing module, or to change the category of a module. In a suitable approach, a mouse or other user interface device is used to select a module and to drag the module to the new location, e.g. using a "drag-and-drop" mouse operation, as shown in the example of FIG. 16. Similarly, dragging and dropping a module from the "Selected Modules" sub-window to the "All Modules" sub-window chooses to remove the module from consideration in evaluating the clinical question, while dragging and dropping a module from the "All Modules" sub-window to the "Selected Modules" sub-window acts to order that the module be run. (These are user interface options for implementing the operation 54 shown in FIG. 7, which then updates the patient CQ-M matrix 40).

FIGS. 8-16 are merely illustrative examples, and numerous other user interface features can be incorporated. For example, the modules shown in the "Selected Modules" and "All Modules" sub-windows can be color-coded or otherwise designed to convey information such as the status (e.g. executed, in-progress, not executed), and/or can be constructed as "live icons" that display summary information pertaining to the output of the module. In some embodiments, a mapping program may be accessed to plot geographical locations of clinical trials (e.g., mined from the clinicaltrial.gov database) in conjunction with a module whose output indicates patient eligibility for such clinical trials. In some user interface embodiments, the outputs of two or more modules can be displayed simultaneously. The linking of such modules can be implemented using a module-module matrix (M-M matrix) or can be implemented directly in the CQ-M matrix using suitable fields in the module descriptions. When a module is added or updated, either by the clinician via operation 54 or by otherwise-generated changes 64 (see FIG. 7), it is optionally highlighted as a new or updated module by a red outline, flashing, or other suitable indication.

The disclosed clinical decision support systems employs analytical modules in the context of clinical questions via the CQ-M matrix. In this environment, patient subgroups can be tracked and captured through CQ-M matrix version instances. Cumulative data as well as individualized use cases can be used to disseminate clinical knowledge, best practices or outcomes. Additionally, clinicians can add comments and other notes to modules and/or clinical questions via the comments section or user forum, so that the clinical decision support system provides a social media venue via which clinicians can discuss system components (e.g. modules) in patient-specific and/or public contexts.

The illustrative embodiments are directed to clinical decision support for breast cancer patients. However, the disclosed clinical decision support systems and methods are suitably employed in other contexts, both within oncology and beyond, and may be applied to other data sources such as infectious diseases where clinical reasoning advantageously combines multiple inputs.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A non-transitory storage medium storing instructions executable by an electronic data processing device to perform a clinical decision support method comprising:
   receiving a patient record comprising at least a patient diagnosis and data from one or more tests performed on the patient;
   automatically determining, by the electronic data processing device based on the received patient diagnosis and received data from the one or more tests, a plurality of clinical questions relating to the patient;
   associating a plurality of computer implemented analytical modules with the plurality of automatically determined clinical questions to be answered by the electronic data processing device using one or more analytical modules, wherein the plurality of clinical questions include at least one prognosis or diagnosis clinical question, at least one therapy selection clinical question, at least one therapy response clinical question, and at least one clinical trial selection clinical question, and wherein the associating comprises:
      generating a clinical question module (CQ-M) association data structure for the patient, wherein a different CQ-M association data structure is generated for each different stage of a care cycle; and
      associating, within each of the CQ-M association data structures, each of the plurality of clinical questions with one or more of the plurality of computer implemented analytical modules used to answer the associated clinical questions;
   computing, by the electronic data processing device, an output of the associated computer implemented analytical module for the patient for each of the plurality of clinical questions for which output can be generated from the received data from the one or more tests;
   displaying information for the patient pertaining to the plurality of clinical questions, comprising the outputs computed for the patient, and further comprising information about the plurality of clinical questions for which no output can be generated from the received data from the one or more tests;
   receiving, from a viewer of the displayed information, modification of one or more analytical modules associated with the plurality of clinical questions for which no output can be generated from the received data from the one or more tests, the modification comprising one or more of: (1) removing an association of a computer implemented analytical module with a clinical question, and (2) associating a computer implemented analytical module with a clinical question with which it was not previously associated by the CQ-M association data structure for the patient.

2. The non-transitory storage medium of claim 1, wherein the computer-implemented analytical modules include at least one module configured to perform an in silico test classifying a cancer sub-type, at least one module configured to perform an in silico test for detecting status of a hormone receptor, at least one module configured to perform an in silico test for detecting fusion genes, and at least one module configured to perform an in silico test predicting a therapy response based on a genetic signature.

3. The non-transitory storage medium of claim 1, wherein the computer implemented analytical modules include a plurality of computer implemented analytical modules configured to perform in silico genetic tests using genetic sequencing or microarray or proteomic data.

4. The non-transitory storage medium of claim 1, wherein:
   the associating further comprises generating a module-module (M-M) association data structure associating modules, and
   the clinical decision support method further comprises, during the computing, identifying missing input data for a computer-implemented analytical module to be computed and computing outputs of computer implemented analytical modules for the patient indicated by the M-M association data structure as providing the missing input data.

5. The non-transitory storage medium of claim 1, further comprising:
   receiving a user request to compute output of a computer implemented analytical module for a patient other than the computer-implemented modules computed by the associating and computing operations; and additionally computing the output of the user-requested computer implemented analytical module.

6. The non-transitory storage medium of claim 1, wherein the clinical decision support method further comprises:
populating the clinical questions with outputs computed for the patient of the computer implemented analytical modules,
wherein the populating re-uses outputs computed for the patient when a computer implemented analytical module is associated with two or more different clinical questions by the CQ-M association data structure for the patient.

7. The non-transitory storage medium of claim 6, wherein the clinical decision support method further comprises:
receiving new or updated information affecting the output computed for the patient of a computer implemented analytical module affected by the new or updated information;
re-computing the output of the affected computer implemented analytical module for the patient based on the new or updated information; and re populating each clinical question associated with the affected computer implemented analytical module by the CQ-M association data structure for the patient.

8. The non-transitory storage medium of claim 6, wherein the clinical decision support method further comprises:
receiving new or updated information that updates a clinical question; and
modifying the CQ-M association data structure to modify the analytical modules associated with the updated clinical question based on the new or updated information.

9. The non-transitory storage medium of claim 8, wherein:
the receiving of new or updated information comprises generating an answer for the updated clinical question; and
the modifying of the CQ-M association data structure comprises removing analytical modules not related to the answer to the updated clinical question.

10. The non-transitory storage medium of claim 1, wherein the generating comprises:
copying a template CQ-M association data structure to generate the CQ-M association data structure for the patient.

11. The non-transitory storage medium of claim 10, wherein the clinical decision support method further comprises:
providing a user interface via which the user modifies the CQ-M association data structure for the patient, and
updating the populating based on the modified CQ-M association data structure for the patient.

12. The non-transitory storage medium of claim 11, wherein the user interface enables the user to modify the CQ-M association data structure for the patient.

13. The non-transitory storage medium of claim 11, wherein the user interface provides two or more display areas containing icons representing computer implemented analytical modules of different categories, and enables the user to modify the CQ-M association data structure for the patient by dragging and dropping an icon from one display area into another display area.

14. The non-transitory storage medium of claim 11, wherein:
the user interface enables the user to select a clinical question and said selection causes the user interface to display icons representing analytical modules associated by the CQ-M association data structure with the user selected clinical question, and
the user interface enables the user to select an analytical module associated by the CQ-M association data structure with the user selected clinical question by selecting its displayed icon and selection of the selected analytical module causes the user interface to display a window containing output generated by the selected analytical module.

15. The non-transitory storage medium of claim 14, wherein the user interface enables the user to select a second analytical module associated by the CQ-M association data structure with the user selected clinical question by selecting its displayed icon and said selection of the second analytical module causes the user interface to display a second window containing output generated by the second analytical module while continuing to display the window containing output generated by the first selected analytical module.

16. The non-transitory storage medium of claim 14, wherein the user interface is configured to limit the clinical questions available for user selection based on a current state of a workflow care cycle assigned to the patient.

17. The non-transitory storage medium of claim 16, wherein:
the clinical questions include at least one prognosis or diagnosis clinical question, at least one therapy selection clinical question, and at least one therapy response clinical question,
the workflow care cycle includes ordered stages (1) screening, (2) prognosis or diagnosis, (3) therapy selection, and (4) therapy response, and (5) monitoring the user interface is configured to limit the clinical questions available for user selection to the at least one prognosis or diagnosis clinical question stage (1) and to the at least one prognosis or diagnosis clinical question and the at least one therapy selection clinical question in stage (2).

18. The non-transitory storage medium of claim 14, wherein the user interface enables the user to update the CQ-M association data structure by moving an icon representing an analytical module from a display region grouping icons of one category to a display region grouping icons of a different category.

19. The non-transitory storage medium of claim 11, wherein the clinical decision support method further comprises:
storing a record of user operations performed via the user interface;
generating a processing pipeline corresponding to the stored user operations; and
applying the processing pipeline to a different patient.

20. The non-transitory storage medium of claim 11, wherein the clinical decision support method further comprises:
storing a record of user operations performed via the user interface to generate an audit trail; and
generating a clinical report based on the audit trail.

21. The non-transitory storage medium of claim 1, wherein the displaying further includes:
displaying a comment section or user forum; and
enabling a user to add commentary to the comment section or user forum.

22. A clinical decision support method, comprising:
receiving, by a computer, a patient record comprising at least a patient diagnosis and data from one or more tests performed on the patient;

automatically determining, by the computer based on the received patient diagnosis and received data from the one or more tests, a plurality of clinical questions relating to the patient, wherein output can be generated by the computer for some of the automatically determined plurality of clinical questions relating to the patient based on the received patient diagnosis and received data from the one or more tests, and wherein output cannot be generated by the computer for some of the automatically determined plurality of clinical questions relating to the patient based on the received patient diagnosis and received data from the one or more tests;

computing, by the computer, outputs for the patient of a plurality of computer implemented analytical modules associated with the plurality of automatically determined clinical questions by a clinical question-module (CQ-M) matrix having one of rows and columns representing the clinical questions and the other of rows and columns representing the computer implemented analytical modules, wherein a different CQ-M matrix is generated for each different stage of a care cycle, and wherein the clinical questions of the CQ-M matrix include at least one prognosis or diagnosis clinical question, at least one therapy selection clinical question, and at least one therapy response clinical question;

displaying a list of the clinical questions including the at least one prognosis or diagnosis clinical question, the at least one therapy selection clinical question, and the at least one therapy response clinical question;

receiving a selection of a listed clinical question via the computer; and displaying information for the patient pertaining to the selected clinical question comprising outputs computed for the patient of one or more computer implemented analytical modules associated with the selected clinical question, and further displaying information about the plurality of clinical questions for which no output can be generated from the received patient diagnosis and received data from the one or more tests.

23. The clinical decision support method of claim 22, wherein the computer-implemented analytical modules include a plurality of computer-implemented analytical modules configured to perform in silico genetic tests.

24. The clinical decision support method of claim 22, further comprising:
receiving new or updated information;
re-computing the outputs for the patient of the one or more computer implemented analytical modules associated with the selected clinical question based on the new or updated information; and
re-displaying the information for the patient pertaining to the selected clinical question comprising the outputs re-computed for the patient based on the new or updated information of the one or more computer implemented analytical modules associated with the selected clinical question.

25. The clinical decision support method of claim 22, further comprising:
displaying a comment section or user forum together with the displayed information for the patient pertaining to the selected clinical question;
receiving commentary from a user;
updating the comment section or user forum to include the received commentary; and
updating the displaying of the comment section or user forum to display the updated comment section or user forum.

26. The clinical decision support method of claim 22, wherein the clinical questions pertain to breast cancer.

27. A clinical decision support method, comprising:
receiving a patient record comprising at least a patient diagnosis and data from one or more tests performed on the patient;
automatically determining, by a computer based on the received patient diagnosis and received data from the one or more tests, a plurality of clinical questions relating to the patient, wherein output can be generated by the computer for some of the automatically determined plurality of clinical questions relating to the patient based on the received patient diagnosis and received data from the one or more tests, and wherein output cannot be generated by the computer for some of the automatically determined plurality of clinical questions relating to the patient based on the received patient diagnosis and received data from the one or more tests;
computing outputs by the computer for the patient of a plurality of computer implemented analytical modules associated with the automatically determined clinical questions including at least one therapy selection clinical question;
generating a clinical question module (CQ-M) data structure for the patient having one of rows and columns representing the clinical questions and the other of rows and columns representing the computer implemented analytical modules, wherein the CQ-M data structure associates the computer implemented analytical modules with the clinical questions to be answered using the associated analytical modules including the at least one therapy selection clinical question, and wherein a different CQ-M data structure is generated for each different stage of a care cycle;
displaying a list of the clinical questions;
receiving a selection of a listed clinical question; and
displaying information for the patient pertaining to the selected clinical question comprising outputs computed for the patient of one or more computer implemented analytical modules associated with the selected clinical question, wherein the displaying of information for the patient pertaining to the selected clinical question includes identifying the one or more computer implemented analytical modules associated with the selected clinical question using the CQ-M data structure for the patient, and further displaying information about the plurality of clinical questions for which no output can be generated from the received patient diagnosis and received data from the one or more tests.

28. The clinical decision support method of claim 27, wherein the generating comprises:
copying a default CQ-M data structure to generate the CQ-M data structure for the patient.

29. The clinical decision support method of claim 28, further comprising:
receiving a modification of the CQ-M data structure for the patient from a user; and
updating the displaying to comprise outputs computed for the patient of one or more computer implemented analytical modules associated by the modified CQ-M data structure with the selected clinical question.

30. The clinical decision support method of claim 29, wherein the receiving comprises:
- displaying two or more display areas containing icons representing computer implemented analytical modules of different categories;
- receiving a drag and drop operation transferring an icon from one display area to another display area; and
- determining the modification of the CQ-M data structure for the patient based on the received drag and drop operation.

* * * * *